United States Patent [19]

Lok et al.

[11] Patent Number: 4,824,554
[45] Date of Patent: Apr. 25, 1989

[54] PROCESSES FOR THE USE OF COBALT-ALUMINUM-PHOSPHORUS-SILICON-OXIDE MOLECULAR SIEVE COMPOSITIONS

[75] Inventors: Brent M. Lok, New City; Bonita K. Marcus, Rye; Edith M. Flanigen, White Plains, all of N.Y.

[73] Assignee: UOP, Des Plains, Ill.

[21] Appl. No.: 149,590

[22] Filed: Jan. 28, 1988

Related U.S. Application Data

[62] Division of Ser. No. 600,174, Apr. 13, 1984, Pat. No. 4,744,970.

[51] Int. Cl.$^4$ .................. C10G 47/02; C07C 2/68; C07C 4/12
[52] U.S. Cl. ..................... 208/46; 208/111; 208/114; 208/137; 208/143; 208/264; 585/466; 585/418; 585/481; 585/527; 585/740
[58] Field of Search ................ 208/46, 111, 114, 143, 208/137, 264; 585/466, 418, 481, 527, 740

[56] References Cited

U.S. PATENT DOCUMENTS

| | | |
|---|---|---|
| 3,769,386 | 10/1973 | Rundell et al. ............ 423/263 |
| 3,941,871 | 3/1976 | Dwyer et al. .............. 423/326 |
| 4,061,724 | 12/1977 | Grose et al. .............. 423/335 |
| 4,310,440 | 1/1982 | Wilson et al. ............ 252/435 |
| 4,420,467 | 12/1983 | Whittam ................... 423/328 |
| 4,440,871 | 4/1984 | Lok et al. ................ 502/214 |
| 4,456,582 | 6/1984 | Marosi et al. ............ 423/277 |
| 4,486,397 | 12/1984 | Eshraghi et al. .......... 423/306 |
| 4,500,651 | 2/1985 | Lok et al. ................ 502/208 |
| 4,554,143 | 11/1985 | Messina et al. ........... 423/306 |
| 4,567,029 | 1/1986 | Wilson et al. ............ 423/306 |

FOREIGN PATENT DOCUMENTS

| | | |
|---|---|---|
| 0054364 | 6/1982 | European Pat. Off. . |
| 0055529 | 7/1982 | European Pat. Off. . |
| 0059059 | 9/1982 | European Pat. Off. . |
| 0055046 | 6/1986 | European Pat. Off. . |
| 984502 | 2/1965 | United Kingdom ........ 423/328 M |

Primary Examiner—Curtis R. Davis
Attorney, Agent, or Firm—Norman L. Balmer

[57] ABSTRACT

Crystalline molecular sieves having three-dimensional microporous framework structures of $CoO_2$, $AlO_2$, $SiO_2$, $PO_2$ and tetrahedral units are disclosed. These molecular sieves have an empirical chemical composition on an anhydrous basis expressed by the formula:

$$mR: (Co_wAl_xP_ySi_z)O_2$$

wherein "R" represents at least one organic templating agent present in the intracrystalline pore system; "m" represents the molar amount of "R" present per mole of $(Co_wAl_xP_ySi_z)O_2$; and "w", "x", "y" and "z" represent the mole fractions of cobalt, aluminum, phosphorus and silicon, respectively, present as tetrahedral oxides. Their use as adsorbents, catalysts, etc. is also disclosed.

15 Claims, 3 Drawing Sheets

PROCESSES FOR THE USE OF COBALT-ALUMINUM-PHOSPHORUS-SILICON-OXIDE MOLECULAR SIEVE COMPOSITIONS

This is a divisional of our copending application Ser. No. 600,174, filed Apr. 13, 1984 (now U.S. Pat. No. 4,744,970).

FIELD OF THE INVENTION

The instant invention relates to processes for the use of a novel class of crystalline three-dimensional microporous molecular sieves, and as adsorbents and catalysts. The invention relates to novel cobalt-aluminum-phosphorus-silicon-oxide molecular sieves having cobalt, aluminum, phosphorus and silicon in the form of framework tetrahedral oxides. These compositions may be prepared hydrothermally from gels containing reactive compounds of cobalt, aluminum, phosphorus and silicon capable of forming framework tetrahedral oxides, and preferably at least one organic templating agent which functions in part to determine the course of the crystallization mechanism and the structure of the crystalline product.

BACKGROUND OF THE INVENTION

Molecular sieves of the crystalline aluminosilicate zeolite type are well known in the art and now comprise over 150 species of both naturally occurring and synthetic composition. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6 Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In copending and commonly assigned application Ser. No. 400,438, filed July 26, 1982, (now U.S. Pat. No. 4,440,871) there is described a novel class of silicon-substituted aluminophosphates which are both microporous and crystalline. The materials have a three dimensional crystal framework of $PO_2^+$, $AlO_2^-$ and $SiO_2$ tetrahedral units and, exclusive of any alkali metal or calcium which may optionally be present, an as-synthesized empirical chemical composition on an anhydrous basis of:

$$mR:(Si_xAl_yP_z)O_2$$

where "R" represents at least one organic templating agent present in the intracrystalline pore system; "m" represents the moles of "R" present per mole of $(Si_xAl_yP_z)O_2$ and has a value of from zero to 0.3; the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetraheral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In copending and commonly assigned application Ser. No. 480,738, file Mar. 31, 1983 (now U.S. Pat. No. 4,500,651) there is described a novel class of titanium-containing molecular sieves whose chemical composition in the as-synthesized and anhydrous form is represented by the unit empirical formula:

$$mR:(Ti_xAl_yP_z)O_2$$

wherein "R" represents at least one organic templating agent present in the intracrystalline pore system; "m" represents the moles of "R" present per mole of $(Ti_xAl_yP_z)O_2$ and has a value of between zero and about 5.0; and "x", "y" and "z" represent the mole fractions of titanium, aluminum and phosphorus, respectively, present as tetrahedral oxides.

In copending and commonly assigned application Ser. No. 514,334, filed July 15, 1983 (now U.S. Pat. No. 4,567,029), there is described a novel class of crystalline metal aluminophosphates having three-dimensional microporous framework structures of $MO_2$, $AlO_2$ and $PO_2$ tetrahdedral units and having an empirical chemical composition on an anhydrous basis expressed by the formula:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3; "M" represents at least one metal of the group magnesium, manganese, zinc and cobalt; "x", "y" and "z" represent the mole fraction of the metal "M", aluminum and phosphorus, respectively, present as tetrahedral oxides.

In copending and commonly assigned application Ser. No. 514,335, filed July 15, 1983 (now U.S. Pat. No. 4,683,217), there is described a novel class of crystalline ferroaluminophosphates having a three-dimensional microporous framework structure of $FeO_2$, $AlO_2$ and $PO_2$ tetrahedral units and having an empirical chemical composition on an anhydrous basis expressed by the formula:

$$mR:(Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3; and "x", "y" and "z" represent the mole fractions of the iron, aluminum and phosphorus, respectively, present as tetrahedral oxides.

The instant invention relates to new molecular sieves comprising framework tetrahedral oxides of $CoO_2^{-2}$, $AlO_2^-$, $PO_2^+$ and $SiO_2$.

SUMMARY OF THE INVENTION

The instant invention relates to a new class of molecular sieves having a three-dimensional microporous crystal framework structures of $CoO_2^{-2}$, $AlO_2^-$, $PO_2^+$ and $SiO_2$ tetrahedral oxide units. These new cobalt-aluminum-phosphorus-silicon-oxide molecular sieves exhibit ion-exchange, adsorption and catalytic properties and, accordingly, find wide use as adsorbents and catalysts. The members of this novel class of compositions have crystal framework structures of $CoO_2^{-2}$ (and/or $CoO_2^{-1}$), $AlO_2^-$, $PO_2^+$ and $SiO_2$ tetrahedral units and have an empirical chemical composition on an anhydrous basis expressed by the formula:

$$mR:(Co_wAl_xP_ySi_z)O_2$$

wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represent the mole fractions of cobalt, aluminum, phosphorus and silicon, respectively, present as tetrahedral oxides. The instant molecular sieve compositions are characterized in several ways as distinct from heretofore known molecular sieves, including the aforementioned ternary compositions. The instant molecular sieves are characterized by the enhanced thermal stability of certain species and by the existence of species heretofore unknown for binary and ternary molecular sieves.

The molecular sieves of the instant invention will be generally referred to by the acronym "CoAPSO" to designate the crystal framework of $CoO_2^{-2}$, $AlO_2^-$, $PO_2^+$ and $SiO_2$ tetrahderal oxide units. Actual class members will be identified as structural species by assigning a number to the species and, accordingly, are identified as "CoAPSO-i" wherein "i" is an integer. This designation is an arbitrary one and is not intended to denote structural relationship to another material(s) which may also be characterized by a numbering system.

DETAILED DESCRIPTION OF THE INVENTION

The instant invention relates to a new class of molecular sieves having a three-dimensional microporous crystal framework structures of $CoO_2^{-2}$, $AlO_2^-$, $PO_2^+$ and $SiO_2$ tetrahedral oxide units. Reference to $CoO_2^2$ herein is also meant to include reference to $CoO_2^{-1}$, such that $CoO_2^{-2}$ and/or $CoO_2^{-1}$ tetrahedral oxide units may be present. These new molecular sieves exhibit ion-exchange, adsorption and catalytic properties and accordingly find wide use as adsorbents and catalysts.

Figure 1:
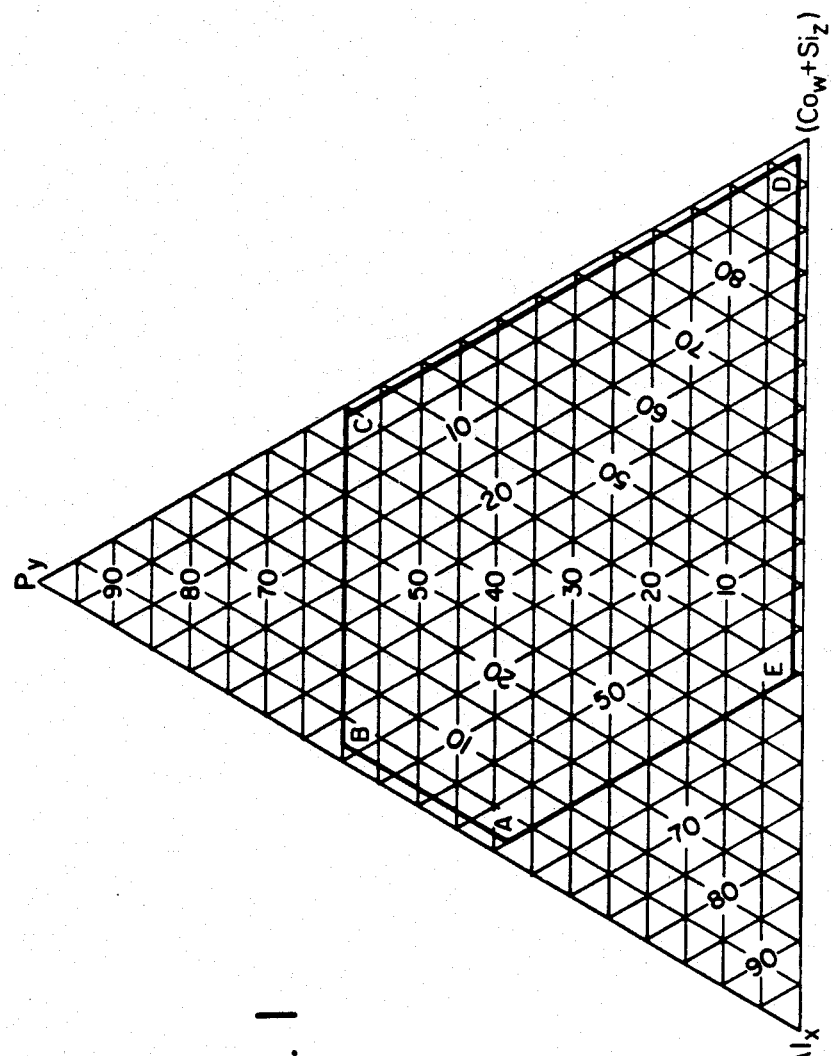
FIG. 1 is a ternary diagram wherein parameters relating to the instant compositions are set forth as mole fractions.

The molecular sieves of the instant invention have three-dimensional microporous framework structures of $CoO_2^{-2}$, $AlO_2^-$, $PO_2^+$ and $SiO_2$ tetrahedral units and have an empirical chemical composition on an anhydrous basis expressed by the formula:

$$mR:(Co_wAl_xP_ySi_z)O_2$$

wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represent the mole fractions of cobalt, aluminum, phosphorus and silicon, respectively, present as tetrahedral oxides, where the mole fractions "w", "x", "y" and "z" are each at least 0.01 and are generally defined, as being within the pentagonal compositional area defined by points A, B, C, D and E of FIG. 1, said points A, B, C, D, and E having the following values for "w", "x", "y" and "z":

| Point | Mole Fraction | | |
|-------|------|------|---------|
|       | x    | y    | (z + w) |
| A     | 0.60 | 0.38 | 0.02    |
| B     | 0.38 | 0.60 | 0.02    |
| C     | 0.01 | 0.60 | 0.39    |
| D     | 0.01 | 0.01 | 0.98    |
| E     | 0.60 | 0.01 | 0.39    |

Figure 2:
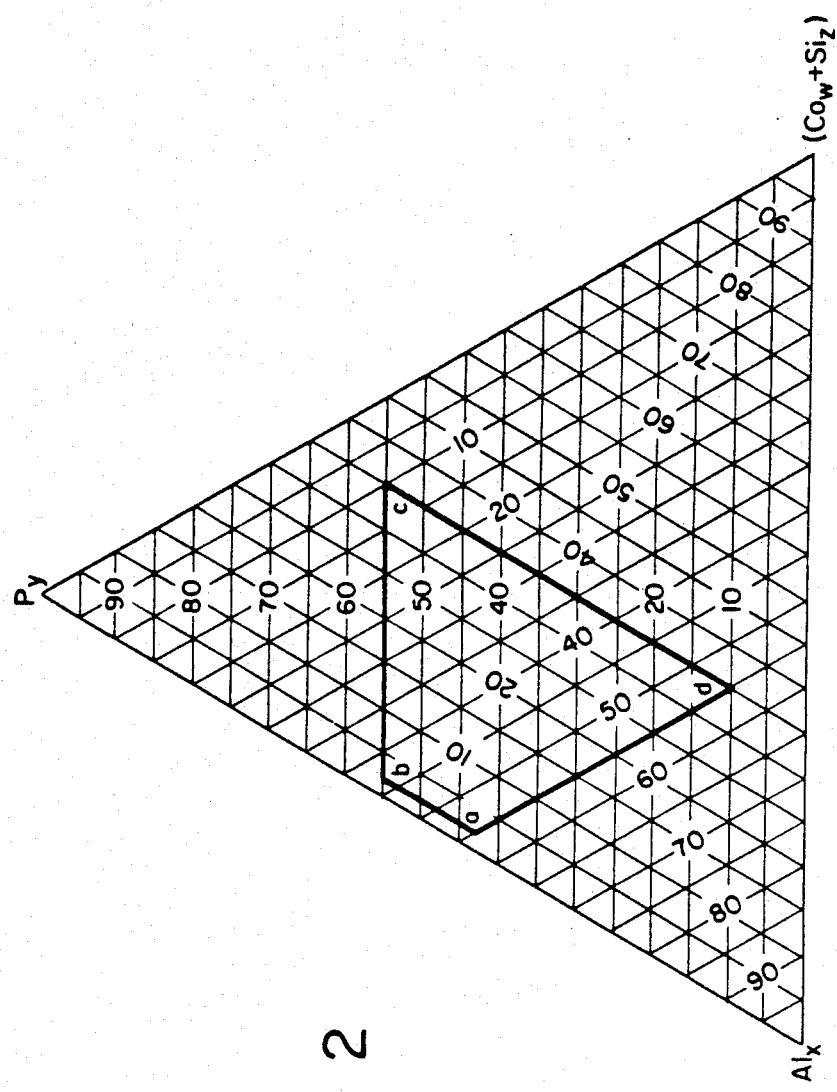
FIG. 2 is a ternary diagram wherein parameters relating to preferred compositions are set forth as mole fractions.

In a preferred subclass of the CoAPSO molecular sieves the values of "w", "x", "y", and "z" in the above formula are within the tetragonal compositional area defined by points a, b, c, and d, of FIG. 2, said points a, b, c, and d having the following values for "w", "x", "y" and "z":

| Point | Mole Fraction | | |
|-------|------|------|---------|
|       | x    | y    | (z + w) |
| a     | 0.55 | 0.43 | 0.02    |
| b     | 0.43 | 0.55 | 0.02    |
| c     | 0.10 | 0.55 | 0.35    |
| d     | 0.55 | 0.10 | 0.35    |

The CoAPSOs of this invention are useful as adsorbents, catalysts, ion-exchangers, and the like in much the same fashion as aluminosilicates have been employed heretofore, although their chemical and physical properties are not necessarily similar to those observed for aluminosilicates.

CoAPSO compositions are generally synthesized by hydrothermal crystallization from a reaction mixture containing reactive sources of cobalt, silicon, aluminum and phosphorus, an organic templating, i.e., structure-directing, agent, preferably a compound of an element of Group VA of the Periodic Table, and optionally an alkali metal. The reaction mixture is generally placed in a sealed pressure vessel, preferably lined with an inert plastic material such as polytetrafluoroethylene and heated, preferably under autogenous pressure at an effective temperature which is generally between 50° C. and 250° C. and preferably between 100° C. and 200° C. until crystals of the CoAPSO product are obtained, usually for an effective time of from several hours to several weeks. Generally the effective crystallization time will be from about 2 hours to about 30 days and typically from about 4 hours to about 20 days. The product is receovered by any convenient method such as centrifugation or filtration.

In synthesizing the CoAPSO compositions of the instant invention, it is preferred to employ a reaction mixture composition expressed in terms of the molar ratios as follows:

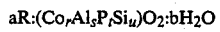

Figure 3:
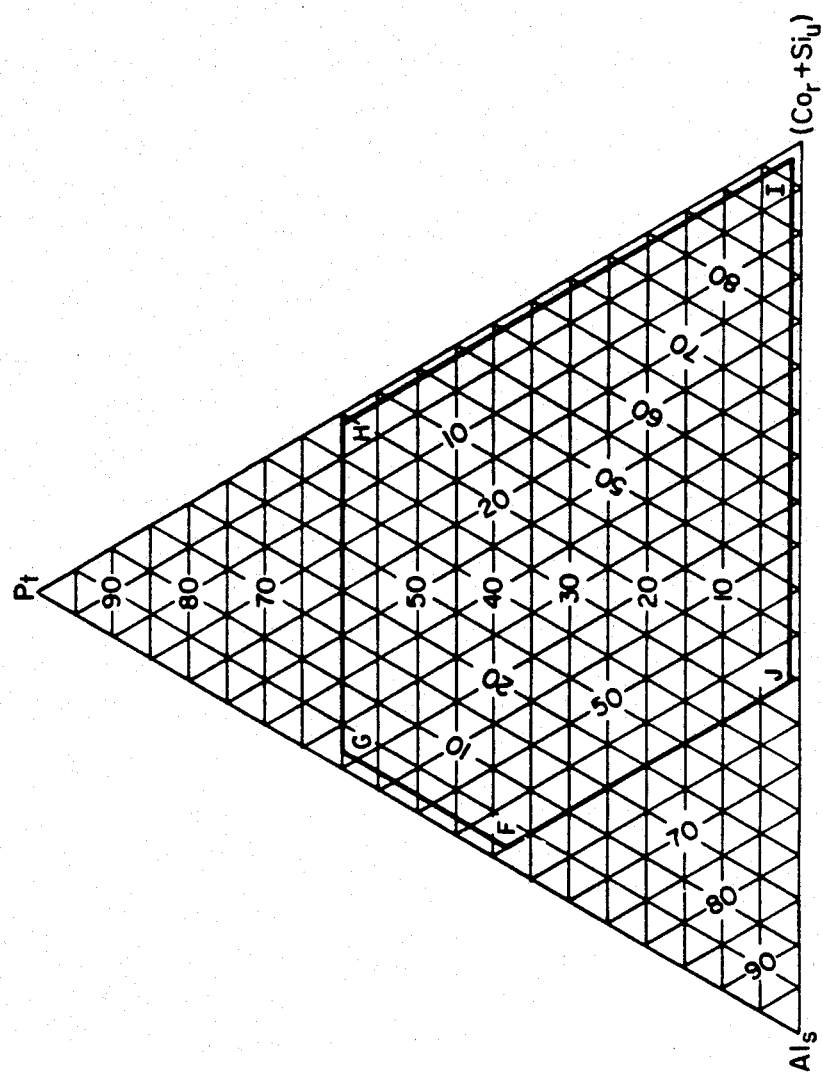
FIG. 3 is a ternary diagram wherein parameters relating to the reaction mixtures employed in the preparation of the compositions of this invention are set forth as mole fractions.

$aR:(Co_rAl_sP_tSi_u)O_2:bH_2O$ wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; and "r", "s", "t" and "u" and represent the mole fractions of cobalt, aluminum, phosphorus and silicon, respectively, and each has a value of at least 0.01. In a preferred embodiment the reaction mixture is selected such that the mole fractions "r", "s", "t" and "u" are generally defined as being within the pentagonal compositional area defined by points E, F, G, H and I of the ternary diagram of FIG. 3. Points E, F, G, H and I of FIG. 3 have the following values for "r", "s", "t" and "u":

| Point | Mole Fraction | | |
|---|---|---|---|
| | s | t | (u + n) |
| F | 0.60 | 0.38 | 0.02 |
| G | 0.38 | 0 60 | 0.02 |
| H | 0.01 | 0.60 | 0.39 |
| I | 0.01 | 0.01 | 0.98 |
| J | 0.60 | 0.01 | 0.39 |

For reasons unknown at present, not every reaction mixture gave crystalline CoAPSO products when reaction products were examined for CoAPSO products by X-ray analysis. Those reaction mixtures from which crystalline CoAPSO products were obtained are reported in the examples hereinafter as numbered examples and those reaction mixtures from which CoAPSO products were not identified by use of X-ray analysis are reported as lettered examples.

In the foregoing expression of the reaction composition, the reactants are normalized with respect to the total of "r", "s", "t" and "u" such that (r+s+t+u)=1.00 mole, whereas in the examples the reaction mixtures are expressed in terms of molar oxide ratios and may be normalized to the moles of $P_2O_5$. This latter form is readily converted to the former form by routine calculations by dividing the number of moles of each component (including the template and water) by the total number of moles of cobalt, aluminum, phosphorus and silicon which results in normalized mole fractions based on total moles of the aforementioned components.

In forming reaction mixtures from which the instant molecular sieves are formed the organic templating agent can be any of those heretofore proposed for use in the synthesis of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium and quaternary ammonium compounds, the latter two being represented generally by the formula $R_4X^+$ wherein "X" is nitrogen or phosphorous and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents can either produce mixtures of the desired CoAPSOs or the more strongly directing templating species may control the course of the reaction with the other templating species serving primarily to establish the pH conditions of the reaction gel. Representative templating agents include: tetramethylammonium; tetraethylammonium; tetrapropylammonium; tetrabutylammonium ions; tetrapentylammonium ions; di-n-propylamine; tripropylamine; triethylamine; triethanolamine; piperidine; cyclohexylamine; 2-methylpyridine; N,N-dimethylbenzylamine; N,N-dimethylethanolamine; chlorine; N,N'-dimethylpiperazine; 1,4-diazabicyclo (2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of CoAPSO, i.e., a single templating agent may, with proper manipulation of the reaction conditions, direct the formation of several CoAPSO compositions, and a given CoAPSO may be produced using several different templating agents.

Most any reactive silicon source may be employed such that $SiO_2$ tetrahedral oxide units are formed in situ. The source of silicon may be silica, either as a silica sol or as fumed silica, a reactive solid amorphous precipitated silica, silica gel, alkoxides of silicon, silicic acid or alkali metal silicate and the like.

The most suitable phosphorus source yet found for the present process is phosphoric acid. but organic phosphates such as triethyl phosphate have been found satisfactory, and so also have crystalline or amorphous aluminophosphates such as the $AlPO_4$ compositions of U.S. Pat. No. 4,310,440. Organo-phosphorus compounds, such as tetrabutylphosphonium bromide, do not apparently serve as reactive sources of phosphorus, but these compounds do function as templating agents. Conventional phosphorus salts such as sodium metaphosphate, may be used, at least in part, as the phosphorus source, but are not preferred.

The preferred aluminum source is either an aluminum alkoxide, such as aluminum isopropoxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The source of cobalt can be introduced into the reaction system in any form which permits the formation in situ of a reactive form of cobalt, i.e., reactive to form the framework tetrhedral unit $CoO_2^{-2}$. Compounds of cobalt which may be employed include oxides, hydroxides, alkoxides, carboxylates, sulfates, nitrates, halides and the like including cobalt chloride hexahydrate, alpha cobaltous iodide, cobaltous sulfate, cobalt acetate, cobaltous bromide and cobaltous chloride.

While not essential to the synthesis of CoAPSO compositions, stirring or other moderate agitation of the reaction mixture and/or seeding the reaction mixture with seed crystals of either the CoAPSO species to be produced or a topologically similar aluminophosphate, aluminosilicate or molecular sieve composition, facilitates the crystallization procedure.

After crystallization the CoAPSO product may be isolated and advantageously washed with water and dried in air. The as-synthesized CoAPSO generally contains within its internal pore system at least one form of the templating agent employed in its formation. Most commonly any organic moiety derived from the organic template is present, at least in part, as a charge-balancing cation as is generally the case with as-synthesized aluminosilicate zeolites prepared from organic-containing reaction systems. It is possible, however, that some or all of the organic moiety is an occluded molecular species in a particular CoAPSO species. As a general rule the templating agent, and hence the occluded organic species, is too large to move freely through the pore system of the CoAPSO product and must be removed by calcining the CoAPSO at temperatures of 200° C. to 700° C. to thermally degrade the organic species. In a few instances the pores of the CoAPSO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the CoAPSO phase wherein the organic moiety occupying the intracrystalline pore system as a result of the hydrothermal crystallization process has been reduced by post-synthesis treatment such that the value of "m" in the composition formula

$$mR:(Co_wAl_xP_ySi_z)O_2$$

has a value of less than 0.02. The other symbols of the formula are as defined hereinabove. In those preparations in which an alkoxide is employed as the source of cobalt, aluminum, phosphorous or silicon the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized CoAPSO material.

Since the present CoAPSO compositions are formed from $CoO_2$, $AlO_2$, $PO_2$ and $SiO_2$ tetrahedral units which, respectively, have a net charge of $-2$ (and/or $-1$), $-1$, $+1$ and 0, the matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^+$ tetrahedron or a simple cation such as an alkali metal cation, a cation of cobalt present in the reaction mixture, or an organic cation derived from the templating agent. Similarly, $CoO_2^{-2}$ and/or $CoO_2^{-1}$ tetrahedra can be balanced electrically by association with $PO_2^+$ tetrahedra, a cation of the cobalt, organic cations derived from the templating agent, a simple cation such as an alkali metal cation, or other divalent or polyvalent metal cations introduced from an extraneous source. It has also been postulated that non-adjacent $AlO_2^-$ and $PO_2^+$ tetrahedral pairs can be balanced by $Na^+$ and $OH^-$ respectively [Flanigen and Grose, Molecular Sieve Zeolites-I, ACS, Washington, DC (1971)]

The CoAPSO compositions of the present invention may exhibit cation-exchange capacity when analyzed using ion-exchange techniques heretofore employed with zeolitic aluminosilicates and have pore diameters which are inherent in the lattice structure of each species and which are at least about 3 Å in diameter. Ion exchange of CoAPSO compositions is ordinarily possible only after the organic moiety present as a result of synthesis has been removed from the pore system. Dehydration to remove water present in the as-synthesized CoAPSO compositions can usually be accomplished, to some degree at least, in the usual manner without removal of the organic moiety, but the absence of the organic species greatly facilitates adsorption and desorption procedures. The CoAPSO materials have various degrees of hydrothermal and thermal stability, some being quite remarkable in this regard, and function well as molecular sieve adsorbents and hydrocarbon conversion catalysts or catalyst bases.

In each example a stainless steel reaction vessel was utilized and was lined with an inert plastic material, polytetrafluoroethylene, to avoid contamination of the reaction mixture. In general, the final reaction mixture from which each CoAPSO composition is crystallized is prepared by forming mixtures of less than all of the reagents and thereafter incorporating into these mixtures additional reagents either singly or in the form of other intermediate mixtures of two or more reagents. In some instance the admixed reagents retain their identity in the intermediate mixture and in other cases some or all of the reagents are involved in chemical reactions to produce new reagents. The term "mixture" is applied in both cases. Further, unless otherwise specified, each intermediate mixture as well as the final reaction mixture was stirred until substantially homogeneous.

X-ray patterns of reaction products are obtained by X-ray analysis using standard X-ray powder diffraction techniques. The radiation source is a high-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as 2θ where θ is the Bragg angle as observed on the strip chart. Intensities are determined from the heights of diffraction peaks after subtracting background, "I₀" being the intensity of the strongest line or peak, and "I" being the intensity of each of the other peaks. Alternatively, the X-ray patterns are obtained from the copper K-alpha radiation by use of computer based techniques using Siemens D-500 X-ray powder diffractometers and Siemens Type K-805 X-ray sources, available from Siemens Corporation, Cherry Hill, N.J., with appropriate computer interface.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak, respectively.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their x-ray powder diffraction patterns and such may have one of the x-ray patterns set forth in the following Tables A through M, wherein said x-ray patterns are for both the as-synthesized and calcined forms unless otherwise noted:

TABLE A

| 2θ | d (Å) (CoAPSO-5) | Relative Intensity |
|---|---|---|
| 7.3–7.5 | 12.11–11.79 | m–vs |
| 14.7–14.9 | 6.03–5.95 | w–m |
| 19.6–19.8 | 4.53–4.48 | w–m |
| 20.9–21.2 | 4.25–4.19 | w–vs |
| 22.3–22.4 | 3.99–3.97 | m–vs |
| 25.8–26.0 | 3.453–3.427 | vw–m |

TABLE B

| 2θ | d (Å) (CoAPSO-11) | Relative Intensity |
|---|---|---|
| 7.9–8.1 | 11.19–10.92 | m |
| 9.3–9.5 | 9.51–9.31 | m–s |
| 21.0–21.3 | 4.23–4.17 | vs |
| 22.1–22.3 | 4.02–3.99 | m |
| 22.7–23.1 | 3.92–3.85 | m |
| 23.2–23.4 | 3.83–3.80 | m |

TABLE C

| 2θ | d (Å) (CoAPSO-16) | Relative Intensity |
|---|---|---|
| 11.4–11.6 | 7.76–7.63 | w–s |
| 17.2–17.4 | 5.16–5.10 | m |
| 18.7–18.9 | 4.75–4.70 | vw–m |
| 21.9–22.1 | 4.06–4.02 | vs |
| 23.1–23.3 | 3.85–3.82 | m |
| 26.8–27.0 | 3.326–3.302 | m |
| 29.8–29.9 | 2.998–2.988 | w–m |

TABLE D

| 2θ | d (Å) (CoAPSO-20) | Relative Intensity |
|---|---|---|
| 13.9–14.0 | 6.37–6.33 | m |
| 19.7–19.8 | 4.51–4.48 | m |
| 24.2–24.3 | 3.68–3.66 | vs |
| 28.0–28.1 | 3.187–3.175 | w |
| 31.4–31.5 | 2.849–2.840 | w |
| 34.5–34.6 | 2.600–2.592 | w |

TABLE E

| 2θ | d (Å) (CoAPSO-31) | Relative Intensity |
|---|---|---|
| 8.5–8.6 | 10.40–10.28 | m |
| 20.2–20.3 | 4.40–4.37 | m |
| 22.0–22.1 | 4.04–4.02 | m |
| 22.6–22.7 | 3.93–3.92 | vs |
| 28.0–28.1 | 3.187–3.175 | w |
| 31.7–31.8 | 2.823–2.814 | m |

TABLE F

| 2θ | d (Å) (CoAPSO-34) | Relative Intensity |
|---|---|---|
| 9.4–9.8 | 9.41–9.03 | s–vs |
| 12.86–13.06 | 6.86–6.76 | w |
| 14.08–14.30 | 6.28–6.19 | w–m |
| 15.90–16.20 | 5.57–5.47 | vw–m |
| 20.60–20.83 | 4.31–4.26 | w–vs |
| 30.50–30.80 | 2.931–2.903 | w–m |

TABLE G

| 2θ | d (Å) (CoAPSO-35) | Relative Intensity |
|---|---|---|
| 10.9–11.0 | 8.12–8.04 | m–vs |
| 13.4–13.7 | 6.61–6.46 | m–vs |
| 17.3–17.4 | 5.13–5.10 | m–s |
| 20.9–21.2 | 4.25–4.19 | m |
| 21.9–22.3 | 4.06–3.99 | m–vs |
| 28.3–28.6 | 3.153–3.121 | m |

TABLE H

| 2θ | d (Å) (CoAPSO-36) | Relative Intensity |
|---|---|---|
| 7.8–8.0 | 11.33–11.05 | vs |
| 8.2–8.3 | 10.78–10.65 | m |
| 16.4–16.6 | 5.40–5.34 | m |
| 19.0–19.3 | 4.67–4.60 | m |
| 20.7–21.0 | 4.29–4.23 | m |
| 22.3–22.6 | 3.99–3.93 | w–m |

TABLE J

| 2θ | d (Å) (CoAPSO-39) | Relative Intensity |
|---|---|---|
| 9.4–9.5 | 9.41–9.31 | m |
| 13.3–13.4 | 6.66–6.61 | m |

TABLE J-continued

(CoAPSO-39)

| 2θ | d (Å) | Relative Intensity |
|---|---|---|
| 18.1–18.2 | 4.90–4.87 | w–m |
| 21.0–21.2 | 4.23–4.19 | vs |
| 22.4–22.5 | 3.97–3.95 | m–s |
| 26.4–26.5 | 3.376–3.363 | m |

TABLE K

(CoAPSO-44)

| 2θ | d (Å) | Relative Intensity |
|---|---|---|
| 9.3–9.5 | 9.51–9.31 | vs |
| 16.0–16.3 | 5.54–5.44 | w–m |
| 20.5–20.8 | 4.33–4.27 | m |
| 24.3–25.1 | 3.66–3.548 | w–m |
| 25.8–26.2 | 3.453–3.401 | w–m |
| 30.7–31.1 | 2.912–2.876 | vw–m |

TABLE L

(CoAPSO-46)

| 2θ | d (Å) | Relative Intensity |
|---|---|---|
| 6.5–6.7 | 13.60–13.19 | w |
| 7.2–7.4 | 12.28–11.95 | w |
| 7.6–7.8 | 11.63–11.33 | vs |
| 21.6–21.7 | 4.11–4.10 | w |
| 27.8–27.9 | 3.209–3.198 | w |

TABLE M

(CoAPSO-47)

| 2θ | d (Å) | Relative Intensity |
|---|---|---|
| 9.4–9.6 | 9.41–9.21 | vs |
| 12.8–13.1 | 6.92–6.76 | w–m |
| 16.0–16.3 | 5.54–5.44 | w–m |
| 20.6–21.0 | 4.31–4.23 | m–vs |
| 25.5–25.9 | 3.493–3.440 | w–m |
| 30.6–31.1 | 2.921–2.876 | w–m |

PREPARATIVE REAGENTS

In the following examples the CoAPSO compositions were prepared using numerous reagents. The reagents employed and abbreviations employed herein, if any, for such reagents are as follows:

(a) Alipro: aluminum isopropoxide;
(b) CATAPAL: Trademark of Condea Corporation for pseudoboehmite;
(c) LUDOX-LS: Trademark of DuPont for an aqueous solution of 30 weight percent $SiO_2$ and 0.1 weight percent $Na_2O$;
(d) Co(Ac)$_2$: cobalt acetate $Co(C_2H_3O_2)_2 \cdot 4H_2O$;
(e) $CoSO_4$: cobalt sulfate $(CoSO_4 \cdot 7H_2O)$;
(f) $H_3PO_4$: 85 weight percent phosphoric acid in water;
(g) TBAOH: tetrabutylammonium hydroxide (25 wt.% in methanol);
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine $(C_7H_{13}N)$;
(k) MQuin: Methyl Quinuclidine hydroxide, $(C_7H_{13}NCH_3OH)$;
(l) C-hex: cyclohexylamine;
(m) TEAOH: tetraethylammonium hydroxide (40 wt.% in water);
(n) DEEA: diethanolamine;
(o) TPAOH: tetrapropylammonium hydroxide (40 wt.% in water); and
(p) TMAOH: tetramethylammonium hydroxide (40 wt.% in water)

PREPARATIVE PROCEDURE

The CoAPSO compositions were prepared by preparing reaction mixtures having a molar composition expressed as:

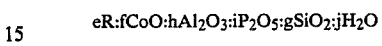

$$eR : fCoO : hAl_2O_3 : iP_2O_5 : gSiO_2 : jH_2O$$

wherein e, f, h, i, g and j represent the moles of template R, cobalt (expressed as the oxide), $Al_2O_3$, $P_2O_5$ ($H_3PO_4$ expressed as $P_2O_5$), $SiO_2$ and $H_2O$, respectively. The values for e, f, h, i, g and j were as set forth in the hereinafter discussed preparative examples.

The reaction mixtures were prepared by forming a starting reaction mixture comprising the $H_3PO_4$ and one half of the water. This mixture was stirred and the aluminum source (Alipro or CATAPAL) added. The resulting mixture was blended until a homogeneous mixture was observed. The LUDOX-LS was then added to the resulting mixture and the new mixture blended until a homogeneous mixture was observed. The cobalt source (Co(Ac)$_2$, CoSO$_4$ or mixtures thereof) was dissolved in the remaining water and combined with the first mixture. The combined mixture was blended until a homogenous mixture was observed. The organic templating agent was added to this mixture and blended for about two to four minutes until a homogenous mixture was observed. The resulting mixture (final reaction mixture) was placed in a lined (polytetrafluoroethylene) stainless steel pressure vessel and digested at a temperature (150° C., 200° C. or 225° C.) for a time. Alternatively, if the digestion temperature was 100° C. the final reaction mixture was placed in a lined (polytetrafluoroethylene) screw top bottle for a time. All digestions were carried out at the autogenous pressure. The products were removed from the reaction vessel cooled and evaluated as set forth hereinafter.

The following examples are provided to further illustrate the invention and are not intended to be limiting thereof:

EXAMPLES 1 TO 31

CoAPSO molecular sieves were prepared according to the above described procedure and the CoAPSO products determined by x-ray analysis. The results of examples 1 to 31 are set forth in Tables I and II. Tables I and II also contain exmaples A to E wherein X-ray analysis of the reaction mixture product did not show CoAPSO products.

In the Tables I and II, the reaction mixtures are described as the ratio of molar oxides:

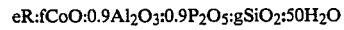

$$eR : fCoO : 0.9Al_2O_3 : 0.9P_2O_5 : gSiO_2 : 50H_2O$$

where "e", "R", "f" and "g" are as above defined. Examples were prepared using this reaction mixture unless otherwise noted in Tables I to II. The values for "e", "f" and "g" are given in Tables I and II.

TABLE I

| Example | Template | e | f | g | Temp (°C.) | Time (days) | CoAPSO Product(s)[1] |
|---|---|---|---|---|---|---|---|
| 1 | Quin | 1 | 0.2 | 0.2 | 150 | 4 | CoAPSO-16; CoAPSO-35 |
| 2 | Quin | 1 | 0.2 | 0.2 | 150 | 10 | CoAPSO-16; CoAPSO-35 |
| 3 | Quin | 1 | 0.2 | 0.2 | 200 | 4 | CoAPSO-16; CoAPSO-35 |
| 4 | Quin | 1 | 0.2 | 0.2 | 200 | 10 | CoAPSO-16; CoAPSO-35 |
| 5 | Quin | 1 | 0.2 | 0.2 | 100 | 4 | CoAPSO-35; CoAPSO-16 |
| 6 | Quin | 1 | 0.2 | 0.2 | 100 | 10 | CoAPSO-16; CoAPSO-35 |
| 7 | MQuin | 1 | 0.2 | 0.2 | 150 | 2 | CoAPSO-35; CoAPSO-17 |
| 8 | MQuin | 1 | 0.2 | 0.2 | 150 | 7 | CoAPSO-35 |
| 9 | MQuin | 1 | 0.2 | 0.2 | 200 | 2 | CoAPSO-35 |
| 10 | MQuin | 1 | 0.2 | 0.2 | 200 | 7 | CoAPSO-35 |
| 11[2,3] | TBAOH | 2 | 0.4 | 0.4 | 200 | 4 | CoAPSO-36; CoAPSO-5 |
| 12[2,3] | TBAOH | 2 | 0.4 | 0.4 | 200 | 10 | CoAPSO-36; CoAPSO-5 |

[1]Major species as identified by x-ray powder diffraction pattern of product, except that when two or more species were identified the species are listed in the order of their predominance in the product.
[2]The molar amount of $Al_2O_3$ was 0.8 instead of 0.9.
[3]Seed crystals of CoAPO-36 were employed in this example, as disclosed in U.S. Ser. No. 514,334, filed July 15, 1983.

TABLE II

| Example | Template | e | f | g | Temp (°C.) | Time (days) | CoAPSO Product(s)[1] |
|---|---|---|---|---|---|---|---|
| 13 | C-hex | 1.0 | 0.2 | 0.6 | 150 | 4 | CoAPSO-44; CoAPSO-5 CoAPSO-13 |
| 14 | C-hex | 1.0 | 0.2 | 0.6 | 150 | 10 | CoAPSO-44; CoAPSO-5 CoAPSO-13 |
| 15 | C-hex | 1.0 | 0.2 | 0.6 | 200 | 4 | CoAPSO-44 |
| 16 | C-hex | 2.0 | 0.2 | 0.6 | 150 | 4 | CoAPSO-44; CoAPSO-13 |
| 17 | C-hex | 2.0 | 0.2 | 0.6 | 150 | 10 | CoAPSO-44; CoAPSO-13 |
| 18 | C-hex | 2.0 | 0.2 | 0.6 | 200 | 4 | CoAPSO-44 |
| 19 | C-hex | 2.0 | 0.2 | 0.6 | 200 | 10 | CoAPSO-44 |
| 20 | Pr$_3$N | 1.0 | 0.2 | 0.2 | 150 | 4 | CoAPSO-5 |
| 21 | Pr$_3$N | 1.0 | 0.2 | 0.2 | 150 | 11 | CoAPSO-5 |
| 22 | Pr$_3$N | 1.0 | 0.2 | 0.2 | 200 | 4 | CoAPSO-5 |
| 23 | Pr$_3$N | 1.0 | 0.2 | 0.2 | 200 | 11 | CoAPSO-5 |
| 24 | Pr$_3$N | 1.0 | 0.2 | 0.2 | 150 | 2 | CoAPSO-5 |
| 25 | Pr$_3$N | 1.0 | 0.2 | 0.2 | 150 | 15 | CoAPSO-5 |
| 26 | Pr$_3$N | 1.0 | 0.2 | 0.2 | 200 | 2 | CoAPSO-5 |
| 27 | Pr$_3$N | 1.0 | 0.2 | 0.2 | 200 | 15 | CoAPSO-5 |
| 28 | Pr$_3$N | 1.0 | 0.2 | 0.2 | 150 | 21 | CoAPSO-5 |
| 29 | Pr$_3$N | 1.5 | 0.2 | 0.2 | 150 | 3 | CoAPSO-5; CoAPSO-36 |
| 30 | Pr$_3$N | 1.5 | 0.2 | 0.2 | 150 | 10 | CoAPSO-5; CoAPSO-36 |
| 31 | Pr$_3$N | 1.5 | 0.2 | 0.2 | 200 | 3 | CoAPSO-5; CoAPSO-36 |
| A* | TBAOH | 2.0 | 0.4 | 0.4 | 150 | 4 | — |
| B* | TBAOH | 2.0 | 0.4 | 0.4 | 150 | 10 | — |
| C | Pr$_3$N | 1.0 | 0.2 | 0.2 | 100 | 4 | — |
| D | Pr$_3$N | 1.0 | 0.2 | 0.2 | 100 | 11 | — |
| E | Pr$_3$N | 1.0 | 0.2 | 0.2 | 200 | 21 | — |

[1]Major species as identified by x-ray powder diffraction pattern of product, except that when two or more species were identified the species are listed in the order of their predominance in the product. A "—" indicates that X-ray analysis failed to show CoAPSO products.
*The molar amount of $Al_2O_3$ was 0.8 instead of 0.9.

EXAMPLES 32 TO 61

Examples 32 to 61 were carried out using di-n-propylamine as the organic templating agent. The preparative procedure was as above described except that in examples 39–45 and 53 to 61 the preparative procedure was modified such that the cobalt acetate was added to the phosphoric acid and water, followed by addition of the aluminum source, silicon source and then the organic templating agent. The aluminum source in examples 32 to 45, 60 and 61 was aluminum isoproxide and in examples 46 to 59 the aluminum source was CATAPAL. The reaction mixtures for examples 32 to 61 are described in terms of the molar oxide ratios:

$$ePr_2NH:0.2CoO:0.9Al_2O_3:0.9P_2O_5:0.2SiO_2:50H_2O$$

where "e" is the moles of template Pr$_2$NH and where "e" was one (1) for examples 32 to 35, 42 to 45, 49 to 52, 56 to 61 and "e" was two (2) for examples 36 to 41, 46 to 48, 53 to 55. Examples F, G, H and I are reaction mixtures where X-ray analysis of the reaction products did not show CoAPSO products. Examples 32 to 61 and F, G, H and I are set forth in Table III.

TABLE III

| Example | Temp (°C.) | Time (days) | CoAPSO Product(s)[1] |
|---|---|---|---|
| 32 | 150 | 4 | CoAPSO-11; CoAPSO-39 |
| 33 | 150 | 11 | CoAPSO-11; CoAPSO-46; CoAPSO-39 |
| 34 | 200 | 4 | CoAPSO-11; CoAPSO-39; CoAPSO-46 |
| 35 | 200 | 11 | CoAPSO-11; CoAPSO-39; CoAPSO-5 |
| 36 | 150 | 10 | CoAPSO-46 |
| 37 | 200 | 4 | CoAPSO-11; CoAPSO-5; CoAPSO-39 |
| 38 | 200 | 10 | CoAPSO-11; CoAPSO-5 |
| 39 | 150 | 10 | CoAPSO-46 |
| 40 | 200 | 4 | CoAPSO-11; CoAPSO-5; CaAPSO-39; CoAPSO-46 |
| 41 | 200 | 10 | CoAPSO-11; CoAPSO-5; CoAPSO-39; CoAPSO-46 |
| 42 | 150 | 4 | CoAPSO-11 |
| 43 | 150 | 11 | CoAPSO-11; CoAPSO-46 |
| 44 | 200 | 4 | CoAPSO-11; CoAPSO-39 |
| 45 | 200 | 11 | CoAPSO-11; CoAPSO-39 |
| 46 | 150 | 4 | CoAPSO-46 |
| 47 | 150 | 10 | CoAPSO-46; CoAPSO-11 |
| 48 | 200 | 4 | CoAPSO-46; CoAPSO-11 |
| 49 | 150 | 10 | CoAPSO-11 |

TABLE III-continued

| Example | Temp (°C.) | Time (days) | CoAPSO Product(s)[1] |
|---|---|---|---|
| 50 | 150 | 4 | CoAPSO-11 |
| 51 | 200 | 10 | CoAPSO-11 |
| 52 | 200 | 4 | CoAPSO-11 |
| 53 | 150 | 10 | CoAPSO-11; CoAPSO-46 |
| 54 | 200 | 4 | CoAPSO-46; CoAPSO-11; CoAPSO-20 |
| 55 | 200 | 10 | CoAPSO-46; CoAPSO-11; CoAPSO-20 |
| 56 | 150 | 4 | CoAPSO-11 |
| 57 | 150 | 10 | CoAPSO-11 |
| 58 | 200 | 4 | CoAPSO-11 |
| 59 | 200 | 10 | CoAPSO-11 |
| 60 | 150 | 4 | CoAPSO-11 |
| 61 | 150 | 4 | CoAPSO-11 |
| F | 100 | 4 | — |
| G | 100 | 11 | — |
| H | 150 | 4 | — |
| I | 150 | 4 | — |

[1]Major species as identified by x-ray powder diffraction pattern of product, except that when two or more species were identified the species are listed in the order of their predominance in the product. A "—" indicates that X-ray analysis failed to show CoAPSO products.

EXAMPLES 62 TO 83

Examples 62 to 83 were carried out according to the preparative procedure employed in examples 1 to 31 except that the organic templating agent was a TEACH (tetraethylammonium hydroxide). The reaction mixtures for examples 62 to 83 were:

1.0TEAOH:fCoO:0.9Al$_2$O$_3$:0.9P$_2$O$_5$:gSiO$_2$:50H$_2$O wherein "f" was 0.2 except that "f" was 0.1 for examples 78 to 79 and was 0.05 for examples 80 to 83; and g was 0.2 for examples 62 to 70 and was 0.6 for examples 71 to 83. The reactive cobalt source was cobalt (II) sulfate for examples 62 to 70 and cobalt (II) acetate for examples 71 to 83.

The resutls of examples 62 to 83 are set forth in Table IV.

TABLE IV

| Example | Temp (°C.) | Time (days) | CoAPSO Product(s)[1] |
|---|---|---|---|
| 62 | 150 | 4 | CoAPSO-34; CoAPSO-5 |
| 63 | 150 | 12 | CoAPSO-34; CoAPSO-5 |
| 64 | 150 | 12 | CoAPSO-34 |
| 65 | 200 | 4 | CoAPSO-34; CoAPSO-5 |
| 66 | 200 | 12 | CoAPSO-5; CoAPSO-34 |
| 67 | 200 | 12 | CoAPSO-34 |
| 68 | 100 | 4 | CoAPSO-34 |
| 69 | 100 | 12 | CoAPSO-34 |
| 70 | 100 | 12 | CoAPSO-34 |
| 71 | 100 | 2 | CoAPSO-34 |
| 72 | 100 | 7 | CoAPSO-34 |
| 73 | 150 | 2 | CoAPSO-34; CoAPSO-5 |
| 74 | 150 | 13 | CoAPSO-34; CoAPSO-5 |
| 75 | 200 | 2 | CoAPSO-5; CoAPSO-34 |
| 76 | 200 | 7 | CoAPSO-5; CoAPSO-34 |
| 77 | 100 | 14 | CoAPSO-34 |
| 78 | 100 | 14 | CoAPSO-34 |
| 79 | 100 | 28 | CoAPSO-34 |
| 80 | 100 | 10 | CoAPSO-34 |
| 81 | 100 | 20 | CoAPSO-34 |
| 82 | 100 | 2 | CoAPSO-34 |
| 83 | 100 | 4 | CoAPSO-34 |

[1]Major species as identified by x-ray powder diffraction pattern of product, except that when two or more species were identified the species are listed in the order of their predominance in the product.

EXAMPLES 84 TO 106

Examples 84 to 106 were carried out according to the preparative procedure employed in examples 1 to 31 except the organic template was as is shown in Table V. The reaction mixture was:

eR:fCoO:0.9Al$_2$O$_5$0.9P$_2$O$_5$:0.6SiO$_2$:50H$_2$O where "e" was one (1) except that "e" was 1.5 for examples 94 to 97 and "e" was 2.0 for Example 104. The results of examples 84 to 106 are set forth in Table V.

TABLE V

| Example | Template | e | f | Temp (°C.) | Time (days) | CoAPSO Product(s)[1] |
|---|---|---|---|---|---|---|
| 84 | TEAOH | 1.0 | 0.025 | 125 | 3 | CoAPSO-34; CoAPSO-18; |
| 85 | TEAOH | 1.0 | 0.025 | 125 | 5 | CoAPSO-34; CoAPSO-5; |
| 86 | TEAOH | 1.0 | 0.025 | 100 | 5 | CoAPSO-34; CoAPSO-5; |
| 87 | TEAOH | 1.0 | 0.025 | 100 | 5 | CoAPSO-34; |
| 88 | TEAOH | 1.0 | 0.025 | 100 | 3 | CoAPSO-34; |
| 89 | TEAOH | 1.0 | 0.025 | 100 | 5 | CoAPSO-34; |
| 90 | TEAOH | 1.0 | 0.025 | 100 | 7 | CoAPSO-34; |
| 91 | Quin | 1.0 | 0.2 | 225 | 5 | CoAPSO-35; CoAPSO-16 |
| 92 | C-hex | 1.0 | 0.2 | 225 | 5 | CoAPSO-5; CoAPSO-44 |
| 93[2] | Pr$_3$N | 1.5 | 0.2 | 150 | 2 | CoAPSO-36; |
| 94[2] | Pr$_3$N | 1.5 | 0.2 | 150 | 7 | CoAPSO-36; |
| 95[2] | Pr$_3$N | 1.5 | 0.2 | 200 | 2 | CoAPSO-36; CoAPSO-5 |
| 96[2] | Pr$_3$N | 1.5 | 0.2 | 200 | 7 | CoAPSO-36; CoAPSO-5 |
| 97[3] | Pr$_2$NH | 1.0 | 0.2 | 150 | 4 | CoAPSO-31; CoAPSO-11 |
| 98[3] | Pr$_2$NH | 1.0 | 0.2 | 150 | 10 | CoAPSO-46; CoAPSO-31 |
| 99[3] | Pr$_2$NH | 1.0 | 0.2 | 200 | 4 | CoAPSO-31; CoAPSO-11 |
| 100[3] | Pr$_2$NH | 1.0 | 0.2 | 200 | 10 | CoAPSO-31; CoAPSO-11; CoAPSO-5; CoAPSO-46 |
| 101[3] | Pr$_2$NH | 1.0 | 0.2 | 150 | 2 | CoAPSO-31 |
| 102[3] | Pr$_2$NH | 1.0 | 0.2 | 150 | 3 | CoAPSO-31 |
| 103[3] | Pr$_2$NH | 1.0 | 0.2 | 200 | 2 | CoAPSO-31; CoAPSO-46 |
| 104 | DEEA | 2.0 | 0.2 | 150 | 2 | CoAPSO-47 |
| 105 | TMAOH | 1.0 | 0.2 | 150 | 4 | CoAPSO-20 |
| 106 | TMAOH | 1.0 | 0.2 | 200 | 4 | CoAPSO-20 |

[1]Major species as identified by x-ray powder diffraction pattern of product, except that when two or more species were identified the species are listed in the order of their predominance in the product.
[2]Seed crystals of CoAPO-36 were employed, as disclosed in U.S. Ser. No. 514,334, filed July 15, 1983.
[3]Seed crystals of AlPO$_4$-31 (U.S. Pat. No. 4,310,440) were employed.

EXAMPLE 107

Samples of the products were subjected to chemical analysis. The chemical analysis for each product is given hereinafter with the example in which the CoAPSO was prepared being given in parenthesis after the designation of the CoAPSO species.

(a) The chemical analysis for CoAPSO-11 (example 35) was:

| Component | Weight Percent |
|---|---|
| $Al_2O_3$ | 31.1 |
| $P_2O_5$ | 46.1 |
| CoO | 6.4 |
| $SiO_2$ | 3.5 |
| Carbon | 5.2 |
| LOI* | 11.7 |

*LOI = Loss on Ignition

The above chemical analysis gives an overall product composition in molar oxide ratios (anhydrous basis) of: $0.085CoO; 0.305Al_2O_3:0.325P_2O_5:0.058SiO_2$; and a formula (anhydrous basis) of:

$$0.07R(Co_{0.06}Al_{0.47}P_{0.46}Si_{0.04})O_2$$

(b) The chemical analysis for CoAPSO-11 (example 42) was:

| Component | Weight Percent |
|---|---|
| $Al_2O_3$ | 32.5 |
| $P_2O_5$ | 44.7 |
| CoO | 4.4 |
| $SiO_2$ | 1.4 |
| Carbon | 3.9 |
| LOI* | 15.7 |

*LOI = Loss on Ignition

The above chemical analysis gives an overall product composition in molar oxide ratios (anhydrous basis) of: $0.059CoO; 0.319Al_2O_3:0.315P_2O_5:0.023SiO_2$; and a formula (anhydrous basis) of:

$$0.05R(Co_{0.04}Al_{0.47}P_{0.47}Si_{0.02})O_2$$

(c) The chemical analysis for CoAPSO-20 (example 106) was:

| Component | Weight Percent |
|---|---|
| $Al_2O_3$ | 27.7 |
| $P_2O_5$ | 37.8 |
| CoO | 4.6 |
| $SiO_2$ | 10.0 |
| Carbon | 9.4 |
| LOI* | 18.4 |

*LOI = Loss on Ignition

The above chemical analysis gives an overall product composition in molar oxide ratios (anhydrous basis) of: $0.061CoO; 0.272Al_2O_3:0.266P_2O_5:0.166SiO_2$; and a formula (anhydrous basis) of:

$$0.20R(Co_{0.05}Al_{0.42}P_{0.41}Si_{0.13})O_2$$

(d) The chemical analysis of CoAPSO-31 (example 101) was:

| Component | Weight Percent |
|---|---|
| $Al_2O_3$ | 32.3 |
| $P_2O_5$ | 42.4 |
| CoO | 4.3 |
| $SiO_2$ | 3.8 |
| Carbon | 2.8 |
| LOI | 16.6 |

*LOI = Loss on Ignition

The above chemical analysis gives an overall product composition in molar oxide ratios (anhydrous basis) of: $0.057CoO; 0.317Al_2O_3:0.299P_2O_5:0.063SiO_2$; and a formula (anhydrous basis) of:

$$0.04R(Co_{0.04}Al_{0.47}P_{0.44}Si_{0.05})O_2$$

(e) The chemical analysis for CoAPSO-34 (example 69) was:

| Component | Weight Percent |
|---|---|
| $Al_2O_3$ | 28.2 |
| $P_2O_5$ | 41.7 |
| CoO | 4.7 |
| $SiO_2$ | 1.1 |
| Carbon | 5.9 |
| LOI* | 23.6 |

*LOI = Loss on Ignition

The above chemical analysis gives an overall product composition in molar oxide ratios (anhydrous basis) of: $0.063CoO; 0.277Al_2O_3:0.294P_2O_5:0.018SiO_2$; and a formula (anhydrous basis) of:

$$0.06R(Co_{0.05}Al_{0.45}P_{0.48}Si_{0.02})O_2$$

(f) The chemical analysis of CoAPSO-34 (example 72) was:

| Component | Weight Percent |
|---|---|
| $Al_2O_3$ | 28.4 |
| $P_2O_5$ | 40.6 |
| CoO | 4.6 |
| $SiO_2$ | 2.2 |
| Carbon | 7.8 |
| LOI* | 23.3 |

*LOI = Loss on Ignition

The above chemical analysis gives an overall product composition in molar oxide ratios of: $0.061CoO; 0.279Al_2O_3:0.282P_2O_5:0.037SiO_2$; and a formula (anhydrous basis) of:

$$0.08R(Co_{0.05}Al_{0.46}P_{0.46}Si_{0.03})O_2$$

(g) The chemical analysis for CoAPSO-34 (example 79) was:

| Component | Weight Percent |
|---|---|
| $Al_2O_3$ | 31.7 |
| $P_2O_5$ | 40.5 |
| CoO | 2.5 |
| $SiO_2$ | 3.4 |
| Carbon | 8.4 |
| LOI* | 20.8 |

*LOI = Loss on Ignition

The above chemical analysis gives an overall product composition in molar oxide ratios of: $0.033CoO:0.311Al_2O_3:0.285P_2O_5:0.057S.iO_2$; and a formula (anhydrous basis) of:

0.09R(Co$_{0.03}$Al$_{0.49}$P$_{0.45}$Si$_{0.05}$)O$_2$ (h) The chemical analysis of CoAPSO-34 (example 81) was:

| Component | Weight Percent |
|---|---|
| Al$_2$O$_3$ | 32.0 |
| P$_2$O$_5$ | 39.6 |
| CoO | 1.2 |
| SiO$_2$ | 2.7 |
| Carbon | 6.4 |
| LOI* | 22.8 |

*LOI = Loss on Ignition

The above chemical analysis gives an overall product composition in most molar oxide ratios of: 0.016CoO; 0.314Al$_2$O$_3$:0.279P$_2$O$_5$:0.045SiO$_2$; and a formula (anhydrous basis) of:

0.07R(Co$_{0.01}$Al$_{0.50}$P$_{0.45}$Si$_{0.04}$)O$_2$ (i) The chemical analysis of CoAPSO-34 (example 83) was:

| Component | Weight Percent |
|---|---|
| Al$_2$O$_3$ | 33.8 |
| P$_2$O$_5$ | 40.6 |
| CoO | 1.6 |
| SiO$_2$ | 2.1 |
| Carbon | 6.6 |
| LOI* | 21.7 |

*LOI = Loss on Ignition

The above chemical analysis gives an overall product composition in molar oxide ratios (anhydrous basis) of:

0.21CoO:0.332Al$_2$O$_3$:0.286P$_2$O$_5$:0.035SiO$_2$;

and a formula (anhydrous basis) of:

0.07R(Co$_{0.02}$Al$_{0.53}$P$_{0.46}$Si$_{0.03}$)O$_2$ (j) The chemical analysis of CoAPSO-34 (example 77) was:

| Component | Weight Percent |
|---|---|
| Al$_2$O$_3$ | 30.1 |
| P$_2$O$_5$ | 41.7 |
| CoO | 4.8 |
| SiO$_2$ | 2.6 |
| Carbon | 9.0 |
| LOI* | 19.5 |

*LOI = Loss on Igntion

The above chemical analysis gives an overall product composition in molar oxide ratios (anhydrous basis) of: 0.064CoO; 0.295Al$_2$O$_3$:0.294P$_2$O$_5$:0.043SiO$_2$; and a formula (anhydrous basis) of:

0.09R(Co$_{0.05}$Al$_{0.46}$P$_{0.46}$Si$_{0.03}$)O$_2$ (k) The chemical analysis of CoAPSO-34 (example 89) was:

| Component | Weight Percent |
|---|---|
| Al$_2$O$_3$ | 31.8 |
| P$_2$O$_5$ | 38.8 |
| CoO | 0.71 |
| SiO$_2$ | 2.2 |
| Carbon | 6.6 |
| LOI* | 24.1 |

*LOI = Loss on Ignition

The above chemical analysis gives an overall product composition in molar oxide ratios (anhydrous basis) of: 0.01CoO; 0.312Al$_2$O$_3$:0.273P$_2$O$_5$:0.037SiO$_2$; and a formula (anhydrous basis) of:

0.07R(Co$_{0.01}$Al$_{0.51}$P$_{0.45}$Si$_{0.03}$)O$_2$ where the value for cobalt is rounded off from 0.008.

(l) The chemical analysis of CoAPSO-34 (example 90) was:

| Component | Weight Percent |
|---|---|
| Al$_2$O$_3$ | 32.4 |
| P$_2$O$_5$ | 39.3 |
| CoO | 0.66 |
| SiO$_2$ | 3.5 |
| Carbon | 7.2 |
| LOI* | 23.5 |

*LOI = Loss on Ignition

The above chemical analysis gives an overall product composition in molar oxide ratios (anhydrous basis) of: 0.009CoO; 0.318Al$_2$O$_3$:0.277P$_2$O$_5$:0.058SiO$_2$; and a formula (anhydrous basis) of:

0.08R(Co$_{0.01}$Al$_{0.51}$P$_{0.44}$Si$_{0.05}$)O$_2$ where the value for cobalt is rounded off from 0.007.

(m) The chemical analysis of CoAPSO-35 (example 10) was:

| Component | Weight Percent |
|---|---|
| Al$_2$O$_3$ | 27.0 |
| P$_2$O$_5$ | 41.6 |
| CoO | 4.3 |
| SiO$_2$ | 4.3 |
| Carbon | 13.0 |
| LOI* | 22.1 |

*LOI = Loss on Ignition

The above chemical analysis gives an overall product composition in molar oxide ratios (anhydrous basis) of: 0.057CoO; 0.265Al$_2$O$_3$:0.290P$_2$O$_5$:0.054SiO$_2$; and a formula (anhydrous basis) of:

0.14R(Co$_{0.05}$Al$_{0.43}$P$_{0.48}$Si$_{0.04}$)O$_2$ (n) The chemical analysis of CoAPSO-36 (example 93) was:

| Component | Weight Percent |
|---|---|
| Al$_2$O$_3$ | 29.5 |
| P$_2$O$_5$ | 39.6 |
| CoO | 5.2 |
| SiO$_2$ | 6.6 |
| Carbon | 3.3 |
| LOI* | 18.5 |

*LOI = Loss on Ignition

The above chemical analysis gives an overall product composition in molar oxide ratios (anhydrous basis) of:

0.069CoO; 0.289Al$_2$O$_3$:0.279P$_2$O$_5$:0.110SiO$_2$; and a formula (anhydrous basis) of:

0.03R(Co$_{0.05}$Al$_{0.44}$P$_{0.42}$Si$_{0.08}$)O$_2$ (o) The chemical analysis of CoAPSO-44 (example 19) was:

| Component | Weight Percent |
|---|---|
| Al$_2$O$_3$ | 26.3 |
| P$_2$O$_5$ | 36.3 |
| CoO | 4.5 |
| SiO$_2$ | 10.0 |
| Carbon | 13.2 |
| LOI* | 22.6 |

*LOI = Loss on Ignition

The above chemical analysis gives an overall product composition in molar oxide ratios (anhydrous basis) of: 0.06CoO; 0.258Al$_2$O$_3$:0.256P$_2$O$_5$:0.166SiO$_2$; and a formula (anhydrous basis) of:

0.18R(Co$_{0.05}$Al$_{0.41}$P$_{0.41}$Si$_{0.13}$)O$_2$ (p) The chemical analysis of CoAPSO-46 (example 36) was:

| Component | Weight Percent |
|---|---|
| Al$_2$O$_3$ | 31.4 |
| P$_2$O$_5$ | 31.5 |
| CoO | 6.2 |
| SiO$_2$ | 2.9 |
| Carbon | 4.2 |
| LOI* | 27.5 |

*LOI = Loss on Ignition

The above chemical analysis gives an overall product composition in molar oxide ratios (anhydrous basis) of: 0.08CoO; 0.31Al$_2$O$_3$:0.22P$_2$O$_5$:0.05SiO$_2$; and a formula (anhydrous basis) of:

0.06R(Co$_{0.07}$Al$_{0.52}$P$_{0.37}$Si$_{0.04}$)O$_2$ (q) The chemical analysis of CoAPSO-47 (example 104) was:

| Component | Weight Percent |
|---|---|
| Al$_2$O$_3$ | 22.7 |
| P$_2$O$_5$ | 39.8 |
| CoO | 8.2 |
| SiO$_2$ | 2.9 |
| Carbon | 11.4 |
| LOI* | 25.2 |

*LOI = Loss on Ignition

The above chemical analysis gives an overall product composition in molar oxide ratios of: 0.109CoO; 0.223Al$_2$O$_3$:0.280P$_2$O$_5$:0.048SiO$_2$; and a formula (anhydrous basis) of:

0.16R(Co$_{0.09}$Al$_{0.38}$P$_{0.48}$Si$_{0.04}$)O$_2$

EXAMPLE 108

EDAX (energy dispersive analysis by x-ray) microprobe analysis in conjunction with SEM (scanning electron microscope) was carried out on clean crystals of CoAPSO products. Analysis of crystals having a morphology characteristic of the CoAPSO compositions noted hereinafter gave the following analysis based on relative peak heights:

(a) CoAPSO-11 (example 42):

| | Average of Spot Probes |
|---|---|
| Co | 1.0 |
| Al | 8.0 |
| P | 10.0 |
| Si | 1.0 |

(b) CoAPSO-20 (example 106):

| | Average of Spot Probes |
|---|---|
| Co | 0.5 |
| Al | 8.0 |
| P | 7.5 |
| Si | 3.4 |

(c) CoApSO-34 (example 69):

| | Average of Spot Probes |
|---|---|
| Co | 0.5 |
| Al | 8.0 |
| P | 10.0 |
| Si | 1.0 |

(d) CoAPSO-35 (example 10):

| | Average of Spot Probes |
|---|---|
| Co | 0.5 |
| Al | 9.0 |
| P | 7.5 |
| Si | 1.0 |

(e) CoAPSO-36 (example 95):

| | Average of Spot Probes |
|---|---|
| Co | 0.6 |
| Al | 9.1 |
| P | 9.4 |
| Si | 2.2 |

(f) CoAPSO-44 (example 16):

| | Average of Spot Probes |
|---|---|
| Co | 1.0 |
| Al | 8.0 |
| P | 8.0 |
| Si | 0.6 |

(g) CoAPSO-47 (example 104):

| | Average of Spot Probes |
|---|---|
| Co | 0.7 |
| Al | 8.4 |
| P | 9.2 |
| Si | 2.8 |

EXAMPLE 109

Samples of the CoAPSO products were tested for adsorption capacities. The CoAPSO products were evaluated in either the as-synthesized form or were calcined in air or nitrogen, to remove at least part of the organic templating agent, as hereinafter set forth. The absorption capacities of each calcined sample were measured using a standard McBain-Bakr gravimetric adsorption apparatus. The samples were activated in a vacuum at 350° C. prior to measurement. The McBain-Bakr data for the aforementioned calcined CoAPSO products were:

| (a) CoAPSO-11 (example 61): | | | | |
|---|---|---|---|---|
| Adsorbate | Kinetic Diameter, Å | Pressure (Torr) | Temp (°C.) | Wt. % Adsorbed* |
| $O_2$ | 3.46 | 106 | −183 | 6.9 |
| $O_2$ | 3.46 | 744 | −183 | 12.1 |
| isobutane | 5.0 | 740 | 24.2 | 3.9 |
| cyclo-hexane | 6.0 | 82 | 23.9 | 13.5 |
| neopentane | 6.2 | 741 | 25.3 | 3.6 |
| $H_2O$ | 2.65 | 4.6 | 24.9 | 7.1 |
| $H_2O$ | 2.65 | 19 | 24.8 | 21.0 |

*calcined in air at 600° C. for 1 hour prior to activation

The above data demonstrate that the pore size of the calcined product is about 6.0 Å.

| (b) CoAPSO-20 (example 106): | | | | |
|---|---|---|---|---|
| Adsorbate | Kinetic Diameter, Å | Pressure (Torr) | Temp (°C.) | Wt. % Adsorbed* |
| $O_2$ | 3.46 | 102 | −183 | 5 |
| $O_2$ | 3.46 | 744 | −183 | 6.4 |
| $H_2O$ | 2.65 | 4.6 | 23.3 | 10 |
| $H_2O$ | 2.65 | 19 | 23.2 | 14 |

*calcined in air at 500° C. for one hour prior to activation.

The above data demonstrate that the pore size of the calcined product is about 3.0 Å.

| (c) CoAPSO-31 (example 102): | | | | |
|---|---|---|---|---|
| Adsorbate | Kinetic Diameter, Å | Pressure (Torr) | Temp (°C.) | Wt. % Adsorbed* |
| $O_2$ | 3.46 | 105 | −183 | 6.9 |
| $O_2$ | 3.46 | 741 | −183 | 12.8 |
| neopentane | 6.2 | 739 | 23.5 | 5.8 |
| $H_2O$ | 2.65 | 4.6 | 23.5 | 5.8 |
| $H_2O$ | 2.65 | 20 | 24.0 | 15.9 |

*calcined in air at 500° C. for 1.5 hrs prior to activation.

The above data demonstrate that the pore size of the calcined product is greater than about 6.2 Å.

| (d) CoAPSO-34 (example 78): | | | | |
|---|---|---|---|---|
| Adsorbate | Kinetic Diameter, Å | Pressure (Torr) | Temp (°C.) | Wt. % Adsorbed* |
| $O_2$ | 3.46 | 103 | −183 | 15.9 |
| $O_2$ | 3.46 | 731 | −183 | 28.2 |
| n-hexane | 4.3 | 103 | 23.9 | 9.8 |
| isobutane | 5.0 | 741 | 23.3 | 1.8 |
| $H_2O$ | 2.65 | 4.6 | 23.9 | 11.3 |
| $H_2O$ | 2.65 | 18.5 | 24.0 | 28.9 |

*calcined in nitrogen at 425° C. for 2 hrs prior to activation.

The above data demonstrate that the pore size of the calcined product is about 4.3 Å.

| (e) CoAPSO-34 (example 89): | | | | |
|---|---|---|---|---|
| Adsorbate | Kinetic Diameter, Å | Pressure (Torr) | Temp (°C.) | Wt. % Adsorbed* |
| $O_2$ | 3.46 | 105 | −183 | 18.6 |
| $O_2$ | 3.46 | 741 | −183 | 28.8 |
| isobutane | 5.0 | 108 | 23.9 | 9.9 |
| n-hexane | 4.3 | 742 | 23.3 | 1.2 |
| $H_2O$ | 2.65 | 4.6 | 23.8 | 10.7 |
| $H_2O$ | 2.65 | 20.0 | 24.0 | 30.1 |

*calcined in air at 600° C. for one hour prior to activation.

| (f) CoAPSO-35 (example 8): | | | | |
|---|---|---|---|---|
| Adsorbate | Kinetic Diameter, Å | Pressure (Torr) | Temp (°C.) | Wt. % Adsorbed* |
| $O_2$ | 3.46 | 103 | −183 | 11.7 |
| $O_2$ | 3.46 | 731 | −183 | 15.5 |
| iso-butane | 5.0 | 741 | 24.5 | 0.6 |
| n-hexane | 4.3 | 103 | 24.4 | 3.5 |
| $H_2O$ | 2.65 | 4.6 | 24.4 | 14.3 |
| $H_2O$ | 2.65 | 18.5 | 23.9 | 22.7 |

*calcined in nitrogen at 500° C. for 2.0 hours prior to activation.

The above data demonstrate that the pore size of the calcined product is about 4.3 Å.

| (g) CoAPSO-44 (example 19): | | | | |
|---|---|---|---|---|
| Adsorbate | Kinetic Diameter, Å | Pressure (Torr) | Temp (°C.) | Wt. % Adsorbed* |
| $O_2$ | 3.46 | 103 | −183 | 24.8 |
| $O_2$ | 3.46 | 731 | −183 | 31.4 |
| n-hexane | 4.3 | 103 | 24.4 | 7.4 |
| isobutane | 5.0 | 741 | 24.5 | 0.3 |
| $H_2O$ | 2.65 | 4.6 | 24.4 | 27.8 |
| $H_2O$ | 2.65 | 18.5 | 23.9 | 35.1 |

*calcined in air at 500° C. for 1.25 hrs. prior to activation.

The above data demonstrate that the pore size of the calcined product is about 4.3 Å.

| (h) CoAPSO-47 (example 104): | | | | |
|---|---|---|---|---|
| Adsorbate | Kinetic Diameter, Å | Pressure (Torr) | Temp (°C.) | Wt. % Adsorbed* |
| $O_2$ | 3.46 | 102 | −183 | 4.1 |
| $O_2$ | 3.46 | 744 | −183 | 4.9 |
| isobutane | 5.0 | 746 | 24.1 | 0.6 |
| n-hexane | 4.3 | 95 | 23.6 | 1.3 |
| $H_2O$ | 2.65 | 4.6 | 23.3 | 9.6 |
| $H_2O$ | 2.65 | 19 | 23.2 | 14.3 |

*calcined in air at 500° C. for 1.5 hrs. prior to activation.

The above data demonstrate that the pore size of the calcined product is about 4.3 Å.

EXAMPLE 110

(a) The as-synthesized CoAPSO-5 of example 76 was subjected to analysis by x-ray. The CoAPSO-5 product was characterized by the x-ray powder diffraction pattern of Table VII below:

TABLE VII

| 2θ | d,(Å) | 100 × I/Io |
|---|---|---|
| 7.4 | 11.95 | 100 |
| 9.6* | 9.21 | 65 |
| 12.9** | 6.86 | 19 |
| 14.1* | 6.28 | 10 |
| 14.9 | 5.95 | 26 |
| 16.0* | 5.54 | 32 |
| 17.8* | 4.98 | 13 |
| 19.8 | 4.48 | 61 |
| 20.5* | 4.33 | 55 |

TABLE VII-continued

| 2θ | d,(Å) | 100 × I/Io |
|---|---|---|
| 21.1 | 4.21 | 74 |
| 22.4** | 3.97 | 94 |
| 23.0* | 3.87 | 10 |
| 24.8 | 3.59 | 16 |
| 25.2* | 3.53 | 16 |
| 26.0** | 3.427 | 42 |
| 27.4* | 3.255 | 13 |
| 28.2* | 3.164 | 10 |
| 29.1 | 3.069 | 19 |
| 29.5* | 3.028 | 10 |
| 30.1 | 2.969 | 29 |
| 30.6* | 2.921 | 23 |
| 31.1* | 2.876 | 19 |
| 33.7** | 2.660 | 10 |
| 34.5** | 2.600 | 19 |
| 37.0 | 2.430 | 7 |
| 37.7 | 2.386 | 16 |
| 41.5 | 2.176 | 7 |
| 42.2 | 2.141 | 8 |
| 43.7 | 2.071 | 7 |
| 44.9** | 2.019 | 7 |
| 47.8** | 1.903 | 10 |
| 48.9* | 1.863 | 10 |
| 55.8 | 1.647 | 10 |

*peak resulting from CoAPSO-34
**peak resulting from CoAPSO-34 and CoAPSO-5

(b) CoAPSO-5, of example 21 was calcined in air at 600° for four hours. The calcined product was characterized by the x-ray powder diffraction pattern of Table VIII below:

TABLE VIII

| 2θ | d,(Å) | I/Io × 100 |
|---|---|---|
| 7.4 | 11.95 | 100 |
| 12.9 | 6.86 | 22 |
| 14.8 | 5.99 | 13 |
| 19.7 | 4.51 | 39 |
| 20.3* | 4.37 | 83 |
| 21.0 | 4.23 | 74 |
| 21.4* | 4.15 | 99 |
| 22.4 | 3.97 | 74 |
| 22.9* | 3.88 | 35 |
| 24.4 | 3.65 | 13 |
| 25.9 | 3.440 | 30 |
| 27.1** | 3.290 | 17 |
| 28.1* | 3.175 | 26 |
| 29.0 | 3.079 | 26 |
| 30.1 | 2.969 | 30 |
| 33.7 | 2.660 | 13 |
| 34.6 | 2.592 | 22 |
| 35.6* | 2.522 | 26 |
| 37.0 | 2.430 | 13 |
| 37.8 | 2.380 | 13 |
| 42.8 | 2.113 | 13 |
| 43.8 | 2.067 | 9 |
| 47.8 | 1.903 | 9 |
| 55.8 | 1.647 | 9 |

*peak from tridynite
**impurity peak (c) The species denominated herein as CoAPSO-5 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" are the mole fractions as above defined with reference to FIG. 1 or FIG. 2; and having in the as-synthesized or calcined form a characteristic x-ray powder diffraction pattern which contains at least the d-spacings set forth in Table XI:

TABLE IX

| 2θ | d,(Å) | Relative Intensity |
|---|---|---|
| 7.3–7.5 | 12.11–11.79 | m–vs |
| 14.7–14.9 | 6.03–5.95 | w–m |
| 19.6–19.8 | 4.53–4.48 | w–m |
| 20.9–21.2 | 4.25–4.19 | w–vs |
| 22.3–22.4 | 3.99–3.97 | m–vs |
| 25.8–26.0 | 3.453–3.427 | vw–m |

(d) The CoAPSO-5 compositions for which x-ray powder diffraction patterns have been obtained to data have patterns which are characterized by the x-ray pattern of Table X:

TABLE X

| 2θ | d,(Å) | I/Io × 100 |
|---|---|---|
| 7.3–7.5 | 12.11–11.79 | 32–100 |
| 12.7–12.9 | 6.97–6.86 | 2–22 |
| 14.7–14.9 | 6.03–5.95 | 10–26 |
| 19.6–19.8 | 4.53–4.48 | 7–39 |
| 20.9–21.2 | 4.25–4.19 | 19–100 |
| 22.3–22.4 | 3.99–3.97 | 25–94 |
| 24.4–24.8 | 3.65–3.59 | 2–16 |
| 25.8–26.0 | 3.453–3.427 | 6–41 |
| 29.0–29.1 | 3.079–3.069 | 3–26 |
| 29.9–30.1 | 2.988–2.969 | 3–30 |
| 33.5–33.7 | 2.667–2.660 | 2–13 |
| 34.4–34.6 | 2.607–2.592 | 4–22 |
| 36.8–37.0 | 2.442–2.430 | 2–13 |
| 37.5–37.8 | 2.398–2.380 | 3–16 |
| 41.4–41.5 | 2.181–2.176 | 1–7 |
| 42.2–42.8 | 2.141–2.113 | 1–13 |
| 43.7–43.8 | 2.071–2.067 | 0–9 |
| 44.9–45.0 | 2.019–2.014 | 1–7 |
| 47.5–47.8 | 1.914–1.903 | 3–10 |
| 55.6–55.8 | 1.653–1.647 | 1–10 |

EXAMPLE 111

(a) The as-synthesized CoAPSO-11 of example 42 was subjected to analysis by x-ray. The CoAPSO-11 product was characterized by the x-ray powder diffraction pattern of Table XI below:

TABLE XI

| 2θ | d,(Å) | 100 × I/Io |
|---|---|---|
| 7.9 | 11.19 | 32 |
| 9.3 | 9.51 | 72 |
| 12.3* | 7.20 | 16 |
| 13.1 | 6.76 | 24 |
| 15.6 | 5.68 | 32 |
| 16.2 | 5.47 | 12 |
| 18.2 | 4.87 | 16 |
| 18.9 | 4.70 | 12 |
| 20.3 | 4.37 | 40 |
| 21.0 | 4.23 | 100 |
| 22.1 | 4.02 | 56 |
| 22.5 | 3.95 | 60 |
| 22.7 | 3.92 | 72 |
| 23.1 | 3.85 | 68 |
| 24.6 | 3.62 | 20 |
| 26.3 | 3.389 | 28 |
| 28.2 | 3.164 | 16 |
| 28.5 | 3.132 | 24 |
| 29.4 | 3.038 | 20 |
| 29.6 | 3.018 | 16 |
| 29.9 | 2.988 | 16 |
| 31.3 | 2.858 | 16 |
| 32.6 | 2.747 | 24 |
| 34.0 | 2.637 | 16 |
| 36.3 | 2.475 | 12 |
| 37.6 | 2.392 | 20 |
| 39.3 | 2.292 | 12 |
| 42.8 | 2.113 | 8 |

TABLE XI-continued

| 2θ | d,(Å) | 100 × I/Io |
|---|---|---|
| 44.8 | 2.023 | 8 |
| 50.5 | 1.807 | 12 |
| 54.4 | 1.687 | 12 |

*peak may contain impurity (b) CoAPSO-11, of example 42 was calcined in air at 600° for 1.5 hours. The calcined product was characterized by the x-ray diffraction powder diffraction pattern of Table XII below:

TABLE XII

| 2θ | d,(Å) | 100 × I/Io |
|---|---|---|
| 8.1 | 10.92 | 70 |
| 9.5 | 9.31 | 83 |
| 13.1 | 6.76 | 26 |
| 13.5 | 6.56 | 30 |
| 15.8 | 5.61 | 56 |
| 18.5* | 4.80 | 17 |
| 19.2 | 4.62 | 13 |
| 20.2 | 4.40 | sh |
| 20.3 | 4.37 | 35 |
| 21.3 | 4.17 | 100 |
| 22.3 | 3.99 | 61 |
| 22.5 | 3.95 | sh |
| 23.0 | 3.87 | 65 |
| 23.4 | 3.80 | 52 |
| 24.3 | 3.66 | 17 |
| 25.1 | 3.548 | 17 |
| 26.5 | 3.363 | 30 |
| 26.6 | 3.351 | sh |
| 28.2 | 3.164 | 13 |
| 28.9 | 3.089 | 26 |
| 29.5 | 3.028 | 17 |
| 30.1 | 2.969 | 13 |
| 30.5 | 2.931 | 17 |
| 31.8 | 2.814 | 17 |
| 32.9 | 2.722 | 22 |
| 34.7 | 2.585 | 13 |
| 36.2 | 2.481 | 13 |
| 37.9 | 2.374 | 17 |
| 38.3 | 2.350 | 17 |
| 39.5 | 2.281 | 9 |

*peak may contain impurity (c) The species denominated herein as CoAPSO-11 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XIII:

TABLE XIII

| 2θ | d,(Å) | Relative Intensity |
|---|---|---|
| 7.9–8.1 | 11.19–10.92 | m |
| 9.3–9.5 | 9.51–9.31 | m–s |
| 21.0–21.3 | 4.23–4.17 | vs |
| 22.1–22.3 | 4.02–3.99 | m |
| 22.7–23.1 | 3.92–3.85 | m |
| 23.2–23.4 | 3.83–3.80 | m |

(d) The CoAPSO-11 compositions for which x-ray powder diffraction patterns have been obtained to date have patterns which are characterized by the x-ray pattern of Table XIV:

TABLE XIV

| 2θ | d,(Å) | 100 × I/Io |
|---|---|---|
| 7.9–8.1 | 11.19–10.92 | 32–70 |
| 9.3–9.5 | 9.51–9.31 | 72–83 |
| 12.3* | 7.20 | 16 |
| 13.1–13.2 | 6.76–6.71 | 16–26 |
| 13.5–13.6 | 6.56–6.51 | 30 |
| 15.6–15.8 | 5.68–5.61 | 32–56 |
| 16.2–16.3 | 5.47–5.44 | 8–12 |
| 18.2–18.5 | 4.87–4.80 | 16–17 |
| 18.9–19.2 | 4.70–4.62 | 12–13 |
| 19.7–20.2 | 4.51–4.40 | sh |
| 20.3 | 4.37 | 35–40 |
| 21.0–21.3 | 4.23–4.17 | 100 |
| 22.1–22.3 | 4.02–3.99 | 56–61 |
| 22.4–22.6 | 3.97–3.93 | sh–60 |
| 22.7–23.1 | 3.92–3.85 | 65–72 |
| 23.2–23.4 | 3.83–3.80 | 52–68 |
| 24.3–24.6 | 3.66–3.62 | 17–20 |
| 25.1 | 3.548 | 17 |
| 26.3–26.5 | 3.389–3.363 | 28–30 |
| 26.6 | 3.351 | sh |
| 28.1–28.2 | 3.175–3.164 | 13–16 |
| 28.5–28.9 | 3.132–3.089 | 24–26 |
| 29.4–29.5 | 3.038–3.028 | 17–20 |
| 29.6–30.5 | 3.018–2.931 | 13–17 |
| 31.3–31.8 | 2.858–2.814 | 16–17 |
| 32.6–32.9 | 2.747–2.722 | 22–24 |
| 34.0–34.7 | 2.637–2.585 | 13–16 |
| 36.2–36.3 | 2.481–2.475 | 12–13 |
| 36.7–37.9 | 2.392–2.374 | 17–20 |
| 38.3–38.4 | 2.350–2.344 | 17–18 |
| 39.3–39.5 | 2.292–2.281 | 9–12 |
| 42.8–42.9 | 2.113–2.108 | 8–9 |
| 44.7–44.8 | 2.027–2.023 | 8–9 |
| 50.5–50.6 | 1.807–1.804 | 9–12 |
| 54.4–54.6 | 1.687–1.681 | 9–12 |

*peak may contain impurity

EXAMPLE 112

(a) The as-synthesized CoAPSO-16 of example 4 was subjected to analysis by x-ray. The CoAPSO-16 product was characterized by the x-ray powder diffraction pattern of Table XV below:

TABLE XV

| 2θ | d,(Å) | 100 × I/Io |
|---|---|---|
| 8.7* | 10.16 | 17 |
| 11.0* | 8.04 | 40 |
| 11.5 | 7.69 | 32 |
| 13.0* | 6.81 | 15 |
| 15.9 | 5.57 | 13 |
| 17.3* | 5.13 | 55 |
| 17.9* | 4.96 | 13 |
| 18.8 | 4.72 | 23 |
| 20.8* | 4.27 | (sh) |
| 21.2* | 4.19 | 40 |
| 22.0** | 4.04 | 100 |
| 23.2** | 3.83 | 21 |
| 23.8* | 3.74 | 11 |
| 25.1* | 3.548 | 9 |
| 26.9** | 3.314 | 23 |
| 28.6* | 3.121 | 26 |
| 28.8* | 3.100 | 26 |
| 29.0 | 3.079 | 15 |
| 29.6 | 3.018 | 11 |
| 29.9 | 2.988 | 15 |
| 32.2* | 2.780 | 34 |
| 32.8 | 2.730 | 9 |
| 34.6** | 2.592 | 13 |
| 35.8* | 2.508 | 11 |
| 37.9 | 2.374 | 9 |
| 40.1 | 2.249 | 9 |
| 42.2* | 2.141 | 11 |
| 43.0* | 2.103 | 9 |

TABLE XV-continued

| 2θ | d,(Å) | 100 × I/Io |
|---|---|---|
| 44.5 | 2.036 | 9 |
| 48.6** | 1.873 | 13 |
| 49.6 | 1.838 | 11 |
| 51.6 | 1.771 | 11 |
| 52.6 | 1.740 | 6 |
| 55.0 | 1.670 | 6 |
| 55.4* | 1.658 | 11 |

*peak resulting from CoAPSO-35
**peak resulting from CoAPSO-16 and CoAPSO-35

(b) The species denominated herein as CoAPSO-16 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amounts of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XVI:

TABLE XVI

| 2θ | d,(Å) | Relative Intensity |
|---|---|---|
| 11.4–11.6 | 7.76–7.63 | w–s |
| 17.2–17.4 | 5.16–5.10 | m |
| 18.7–18.9 | 4.75–4.70 | vw–m |
| 21.9–22.1 | 4.06–4.02 | vs |
| 23.1–23.3 | 3.85–3.82 | m |
| 26.8–27.0 | 3.326–3.302 | m |
| 29.8–29.9 | 2.998–2.988 | w–m |

(c) The CoAPSO-16 compositions for which x-ray powder diffraction patterns have been obtained to date have patterns which are characterized by the x-ray pattern of Table XVII:

TABLE XVII

| 2θ | d,(Å) | 100 × I/Io |
|---|---|---|
| 11.4–11.6 | 7.76–7.63 | 11–79 |
| 17.2–17.4 | 5.16–5.10 | 66–80 |
| 18.7–18.9 | 4.75–4.70 | 7–53 |
| 21.9–22.1 | 4.06–4.02 | 100 |
| 23.1–23.3 | 3.85–3.82 | 21–24 |
| 26.8–27.0 | 3.326–3.302 | 23–28 |
| 29.0 | 3.079 | 14–18 |
| 29.5–29.7 | 3.028–3.008 | 4–15 |
| 29.8–29.9 | 2.998–2.988 | 15–29 |
| 32.7–32.9 | 2.739–2.722 | 3–9 |
| 34.5–34.7 | 2.600–2.585 | 9–13 |
| 37.8–38.0 | 2.380–2.368 | 6–9 |
| 40.0–40.2 | 2.534–2.243 | 1–9 |
| 44.3–44.6 | 2.045–2.032 | 2–9 |
| 48.5–48.7 | 1.877–1.870 | 8–13 |
| 49.5–49.7 | 1.841–1.834 | 8–11 |
| 51.5–51.7 | 1.774–1.768 | 6–11 |
| 52.5–52.7 | 1.743–1.737 | 6–7 |
| 54.9–55.1 | 1.672–1.667 | 1–6 |

EXAMPLE 113

(a) The as-synthesized CoAPSO-20 of example 106 was subjected to analysis by x-ray. The CoAPSO-20 product was characterized by the x-ray powder diffraction pattern of Table XVIII below:

TABLE XVIII

| 2θ | d,(Å) | 100 × I/Io |
|---|---|---|
| 10.293 | 8.5942 | 7 |
| 12.078 | 7.3278 | 1 |
| 13.925 | 6.3595 | 46 |
| 14.376 | 6.1609 | 2 |
| 18.773 | 4.7268 | 2 |
| 19.738 | 4.4977 | 42 |
| 20.507 | 4.3307 | 3 |
| 22.093 | 4.0233 | 3 |
| 24.227 | 3.6735 | 100 |
| 26.363 | 3.3806 | 3 |
| 26.941 | 3.3094 | 3 |
| 28.052 | 3.1808 | 11 |
| 31.442 | 2.8451 | 11 |
| 31.759 | 2.8175 | 2 |
| 31.980 | 2.7985 | 2 |
| 34.523 | 2.5980 | 16 |
| 37.426 | 2.4029 | 1 |
| 40.075 | 2.2499 | 4 |
| 42.614 | 2.1215 | 4 |
| 47.3 | 1.922 | 4 |
| 51.8 | 1.765 | 8 |

(b) CoAPSO-20, of example 106 was calcined in air at 500° for one hour. The calcined product was characterized by the x-ray powder diffraction pattern of Table XIX below:

TABLE XIX

| 2θ | d,(Å) | 100 × I/Io |
|---|---|---|
| 10.6* | 8.39 | 7 |
| 21.1* | 7.30 | 3 |
| 12.2* | 7.24 | 2 |
| 14.0 | 6.33 | 75 |
| 14.8* | 6.01 | 3 |
| 16.1* | 5.51 | 2 |
| 19.8 | 4.48 | 38 |
| 22.2 | 4.01 | 4 |
| 24.3 | 3.66 | 100 |
| 26.7* | 3.344 | 3 |
| 27.6* | 3.227 | 2 |
| 28.1 | 3.173 | 14 |
| 31.5 | 2.839 | 13 |
| 32.2* | 2.781 | 2 |
| 32.4* | 2.764 | 2 |
| 34.6 | 2.593 | 18 |
| 40.2 | 2.244 | 3 |
| 42.5 | 2.127 | 4 |
| 47.3 | 1.922 | 4 |
| 51.8 | 1.765 | 8 |

*impurity peak (c) The species denominated herein as CoAPSO-20 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XX:

TABLE XX

| 2θ | d,(Å) | Relative Intensity |
|---|---|---|
| 13.9–14.0 | 6.37–6.33 | m |
| 19.7–19.8 | 4.51–4.48 | m |

| 2θ | d,(Å) | Relative Intensity |
|---|---|---|
| 24.2–24.3 | 3.68–3.66 | vs |
| 28.0–28.1 | 3.187–3.175 | w |
| 31.4–31.5 | 2.849–2.840 | w |
| 34.5–34.6 | 2.600–2.592 | w |

(d) The CoAPSO-20 compositions for which x-ray powder diffraction patterns have been obtained to date have patterns which care characterized by the x-ray pattern of Table XXI:

TABLE XXI

| 2θ | d,(Å) | 100 × I/Io |
|---|---|---|
| 13.9–14.0 | 6.37–6.33 | 44–75 |
| 19.7–19.8 | 4.51–4.48 | 38–42 |
| 22.1–22.2 | 4.02–4.00 | 3–4 |
| 24.2–24.3 | 3.68–3.66 | 100 |
| 28 0–28.1 | 3.187–3.175 | 11–14 |
| 31.4–31.5 | 2.849–2.840 | 11–12 |
| 34.5–34.6 | 2.600–2.592 | 16–18 |
| 40.1–40.2 | 2.249–2.243 | 3–4 |
| 42.5–42.6 | 2.127–2.122 | 3–4 |
| 47.3–47.4 | 1.922–1.918 | 4–5 |
| 51.8–51.9 | 1.765–1.762 | 8–9 |

EXAMPLE 114

(a) The as-synthesized CoAPSO-31 of example 101 was subjected to analysis by x-ray. The CoAPSO-31 product was characterized by the x-ray powder diffraction pattern of Table XXII below:

TABLE XXII

| 2θ | d,(Å) | 100 × I/Io |
|---|---|---|
| 8.5 | 10.35 | 58 |
| 17.1 | 5.19 | 5 |
| 18.4 | 4.82 | 2 |
| 20.3 | 4.38 | 42 |
| 21.1 | 4.20 | 4 |
| 22.1 | 4.03 | 28 |
| 22.7 | 3.93 | 100 |
| 23.2 | 3.83 | 2 |
| 25.2 | 3.537 | 4 |
| 25.7 | 3.464 | 3 |
| 28.0 | 3.187 | 12 |
| 29.8 | 3.000 | 6 |
| 31.8 | 2.816 | 20 |
| 35.2 | 2.549 | 9 |
| 36.2 | 2.482 | 2 |
| 37.2 | 2.417 | 2 |
| 37.7 | 2.386 | 2 |
| 38.3 | 2.352 | 2 |
| 39.4 | 2.288 | 3 |
| 39.7 | 2.271 | 2 |
| 40.3 | 2.239 | 2 |
| 45.3 | 2.002 | 2 |
| 46.8 | 1.943 | 2 |
| 48.7 | 1.869 | 2 |
| 51.7 | 1.768 | 4 |

(b) CoAPSO-31 of part (a) was calcined in air at 500° for 1.5 hours. The calcined product was characterized by the x-ray powder diffraction pattern of Table XXIII below:

TABLE XXIII

| 2θ | d,(Å) | 100 × I/Io |
|---|---|---|
| 8.5 | 10.36 | 73 |
| 14.8 | 5.99 | 4 |
| 17.1 | 5.19 | 10 |
| 18.4 | 4.81 | 4 |
| 20.3 | 4.37 | 56 |
| 21.4 | 4.15 | 3 |
| 22.1 | 4.03 | 47 |
| 22.7 | 3.93 | 100 |
| 23.4 | 3.80 | 3 |
| 25.2 | 3.530 | 6 |
| 25.7 | 3.464 | 7 |
| 28.0 | 3.184 | 15 |
| 29.8 | 2.300 | 10 |
| 31.0 | 2.885 | 2 |
| 31.8 | 2.813 | 31 |
| 35.2 | 2.548 | 10 |
| 36.3 | 2.476 | 5 |
| 37.3 | 2.409 | 3 |
| 37.7 | 2.385 | 3 |
| 38.3 | 2.348 | 3 |
| 39.4 | 2.287 | 4 |
| 39.7 | 2.270 | 3 |
| 40.3 | 2.237 | 3 |
| 46.7 | 1.944 | 5 |
| 47.6 | 1.910 | 3 |
| 48.7 | 1.868 | 3 |
| 49.3 | 1.849 | 2 |
| 51.7 | 1.768 | 6 |

(c) The species denominated herein as CoAPSO-31 has a three-dimensional microporous crystal framework structure of $CoO_2$, $AlO_2$, $PO_2$ and $SiO_2$ tetrahedral units and has an empirical chemical composition on an anhydrous basis expressed by the formula:

$mR:(Co_wAl_xP_ySi_z)O_2$ where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XXIV:

TABLE XXIV

| 2θ | d,(Å) | Relative Intensity |
|---|---|---|
| 8.5–8.6 | 10.40–10.28 | m |
| 20.2–20.3 | 4.40–4.37 | m |
| 22.0–22.1 | 4.04–4.02 | m |
| 22.6–22.7 | 3.93–3.92 | vs |
| 28.0–28.1 | 3.187–3.175 | w |
| 31.7–31.8 | 2.823–2.814 | m |

(d) The CoAPSO-31 compositions for which x-ray powder diffraction patterns have been obtained to date have patterns which are characterized by the x-ray pattern of Table XXV:

TABLE XXV

| 2θ | d,(Å) | 100 × I/Io |
|---|---|---|
| 8.5–8.6 | 10.40–10.28 | 58–73 |
| 4.7–14.8 | 6.03–5.99 | 2–4 |
| 17.0–17.2 | 5.22–5.16 | 5–10 |
| 18.4–18.5 | 4.82–4.80 | 2–4 |
| 20.2–20.3 | 4.40–4.37 | 42–56 |
| 21.1–21.4 | 4.21–4.15 | 3–4 |
| 22.0–22.1 | 4.04–4.02 | 28–47 |
| 22.6–22.7 | 3.93–3.92 | 100 |
| 23.2–23.4 | 3.83–3.80 | 2–3 |
| 25.1–25.2 | 3.548–3.534 | 4–6 |
| 25.7–25.8 | 3.466–3.453 | 3–7 |
| 28.0–28.1 | 3.187–3.175 | 12–15 |
| 29.7–29.8 | 3.008–2.998 | 6–10 |
| 31.0–31.1 | 2.885–2.876 | 2–4 |
| 31.7–31.8 | 2.823–2.814 | 20–31 |
| 35.2–35.3 | 2.550–2.543 | 9–10 |
| 36.2–36.3 | 2.481–2.475 | 2–5 |

TABLE XXV-continued

| 2θ | d,(Å) | 100 × I/Io |
|---|---|---|
| 37.2–37.3 | 2.417–2.411 | 2–3 |
| 37.7–37.8 | 2.386–2.380 | 2–3 |
| 38.2–38.4 | 2.356–2.344 | 2–3 |
| 39.3–39.4 | 2.292–2.287 | 3–4 |
| 39.6–39.7 | 2.276–2.270 | 2–3 |
| 40.2–40.3 | 2.243–2.238 | 2–3 |
| 45.2–45.3 | 2.006–2.002 | 1–2 |
| 46.7–46.8 | 1.945–1.941 | 2–5 |
| 47.5–47.6 | 1.914–1.910 | 2–3 |
| 48.7–48.8 | 1.870–1.866 | 2–3 |
| 49.2–49.3 | 1.852–1.848 | 1–2 |
| 51.6–51.7 | 1.771–1.768 | 4–6 |

EXAMPLE 115

(a) The as-synthesized CoAPSO-34 of example 90 was subjected to analysis by x-ray. The CoAPSO-34 product was characterized by the x-ray powder diffraction pattern of Table XXVI below:

TABLE XXVI

| 2θ | d,(Å) | 100 × I/Io |
|---|---|---|
| 9.6 | 9.22 | 100 |
| 12.9 | 6.84 | 11 |
| 14.2 | 6.26 | 10 |
| 16.1 | 5.51 | 35 |
| 18.1 | 4.92 | 15 |
| 20.7 | 4.29 | 62 |
| 22.3 | 3.98 | 3 |
| 23.2 | 3.84 | 4 |
| 25.3 | 3.522 | 17 |
| 26.0 | 3.430 | 14 |
| 27.7 | 3.217 | 2 |
| 28.5 | 3.136 | 3 |
| 29.7 | 3.010 | 4 |
| 30.7 | 2.914 | 25 |
| 31.3 | 2.855 | 16 |
| 31.8 | 2.817 | 3 |
| 34.5 | 2.597 | 6 |
| 36.3 | 2.473 | 3 |
| 39.8 | 2.263 | 3 |
| 43.3 | 2.090 | 3 |
| 43.6 | 2.075 | 3 |
| 47.6 | 1.911 | 2 |
| 47.8 | 1.904 | 3 |
| 49.2 | 1.853 | 5 |
| 51.1 | 1.786 | 3 |
| 53.4 | 1.716 | 3 |
| 54.7 | 1.678 | 2 |

(b) CoAPSO-34, of example 90 was calcined in air at 600° for 1 hour. The calcined product was characterized by the x-ray powder diffraction pattern of Table XXVII below:

TABLE XXVII

| 2θ | d,(Å) | 100 × I/Io |
|---|---|---|
| 9.6 | 9.20 | 100 |
| 10.1 | 8.77 | 6 |
| 13.0 | 6.80 | 14 |
| 16.2 | 5.46 | 8 |
| 17.9 | 4.97 | 4 |
| 18.0 | 4.94 | 3 |
| 19.3 | 4.60 | 4 |
| 20.5 | 4.34 | 3 |
| 20.8 | 4.27 | 14 |
| 21.4 | 4.15 | 4 |
| 23.3 | 3.82 | 2 |
| 24.3 | 3.67 | 3 |
| 25.1 | 3.543 | 3 |
| 25.3 | 3.524 | 3 |
| 25.7 | 3.464 | 2 |
| 26.2 | 3.402 | 5 |
| 31.0 | 2.831 | 10 |
| 31.6 | 2.835 | 5 |

TABLE XXVII-continued

| 2θ | d,(Å) | 100 × I/Io |
|---|---|---|
| 31.8 | 2.815 | 3 |

(c) The species denominated herein as CoAPSO-34 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions, being as above defined with reference to FIG. 1 or FIG. 2; and having in the as-synthesized or calcined form a characteristic x-ray powder diffraction pattern which contains at least the d-spacings set forth in Table XXVIII:

TABLE XXVIII

| 2θ | d,(Å) | Relative Intensity |
|---|---|---|
| 9.4–9.8 | 9.41–9.03 | s–vs |
| 12.86–13.06 | 6.86–6.76 | w |
| 14.08–14.30 | 6.28–6.19 | w–m |
| 15.90–16.20 | 5.57–5.47 | vw–m |
| 20.60–20.83 | 4.31–4.26 | w–vs |
| 30.50–30.80 | 2.931–2.903 | w–m |

(d) The CoAPSO-34 compositions for which x-ray powder diffraction patterns have been obtained to date have patterns which are characterized by the x-ray pattern of Table XXIX:

TABLE XXIX

| 2θ | d,(Å) | 100 × I/Io |
|---|---|---|
| 9.4–9.8 | 9.41–9.03 | 87–100 |
| 10.09–10.14 | 8.77–8.72 | 1–6 |
| 12.86–13.06 | 6.86–6.76 | 11–18 |
| 14.08–14.30 | 6.28–6.19 | 10–24 |
| 15.90–16.24 | 5.57–5.47 | 8–35 |
| 17.85–18.05 | 4.97–4.92 | 3–15 |
| 19.13–19.48 | 4.65–4.55 | 1–4 |
| 20.48–20.56 | 4.34–4.33 | sh–3 |
| 20.60–20.83 | 4.31–4.26 | 14–100 |
| 21.41–22.35 | 4.15–3.98 | 3–4 |
| 23.18–23.31 | 3.84–3.82 | 2–3 |
| 24.25–24.53 | 3.67–3.63 | 0–3 |
| 25.13–25.29 | 3.543–3.520 | 3–17 |
| 25.72–25.98 | 3.464–3.430 | 3–14 |
| 26.06–26.19 | 3.414–3.402 | 5–9 |
| 27.73–27.80 | 3.217–3.209 | 2–16 |
| 28.30–28.46 | 3.153–3.136 | 3–9 |
| 29.50–29.68 | 3.028–3.010 | 4–14 |
| 30.50–30.80 | 2.931–2.903 | 12–25 |
| 31.04–31.33 | 2.881–2.855 | 7–16 |
| 31.60–31.79 | 2.831–2.815 | 3–5 |
| 34.40–34.53 | 2.607–2.597 | 5–6 |
| 36.20–36.32 | 2.481–2.473 | 3–8 |
| 38.40–38.60 | 2.314–2.332 | 3–5 |
| 39.70–39.83 | 2.270–2.263 | 3–4 |
| 43.10–43.28 | 2.099–2.090 | sh–6 |
| 43.40–43.61 | 2.015–2.075 | 3–10 |
| 47.40–47.59 | 1.918–1.911 | sh–2 |
| 47.77–47.80 | 1.904–1.903 | 3–10 |
| 49.17–49.20 | 1.853–1.852 | 5–10 |
| 49.90–50.40 | 1.828–1.809 | 0–11 |
| 51.13–51.20 | 1.786–1.784 | 3–10 |
| 53.20–53.39 | 1.722–1.716 | 3–10 |
| 54.60–54.70 | 1.681–1.678 | 2–7 |

TABLE XXIX-continued

| 2θ | d,(Å) | 100 × I/Io |
|---|---|---|
| 55.80–55.90 | 1.647–1.645 | 2–10 |

EXAMPLE 116

(a) The as-synthesized CoAPSO-35 of example 10 was subjected to analysis by x-ray. The CoAPSO-35 product was characterized by the x-ray powder diffraction pattern of Table XXX below:

TABLE XXX

| 2θ | d,(Å) | 100 × I/Io |
|---|---|---|
| 7.9* | 11.19 | 8 |
| 8.6 | 10.28 | 18 |
| 10.9 | 8.12 | 45 |
| 11.6 | 7.63 | 8 |
| 13.4 | 6.61 | 30 |
| 15.9 | 5.57 | 15 |
| 17.3 | 5.13 | 83 |
| 17.8 | 4.98 | 20 |
| 20.9 | 4.25 | 58 |
| 21.9 | 4.06 | 100 |
| 22.7 | 3.92 | 13 |
| 23.3 | 3.82 | 38 |
| 24.9 | 3.58 | 13 |
| 25.6 | 3.480 | 8 |
| 26.9 | 3.314 | 28 |
| 28.3 | 3.153 | 45 |
| 29.1 | 3.069 | 13 |
| 31.4* | 2.849 | 10 |
| 32.2 | 2.780 | 40 |
| 34.3 | 2.614 | 10 |
| 35.2* | 2.550 | 8 |
| 35.9 | 2.501 | 8 |
| 37.8 | 2.380 | 5 |
| 39.4 | 2.287 | 5 |
| 41.9 | 2.156 | 8 |
| 42.6 | 2.122 | 10 |
| 44.6 | 2.032 | 8 |
| 47.8 | 1.903 | 8 |
| 48.6 | 1.873 | 8 |
| 49.8 | 1.831 | 10 |
| 51.2 | 1.784 | 10 |
| 55.7 | 1.650 | 8 |

*impurity peak (b) CoAPSO-35, of example 10 was calcined in air at 500° C. for two hours. The calcined product was characterized by the x-ray powder diffraction pattern of Table XXXI below:

TABLE XXXI

| 2θ | d,(Å) | 100 × I/Io |
|---|---|---|
| 8.7 | 10.16 | 26 |
| 11.0 | 8.04 | 90 |
| 11.8 | 7.50 | 21 |
| 13.7 | 6.46 | 100 |
| 16.2 | 5.47 | 16 |
| 17.4 | 5.10 | 26 |
| 17.6 | 5.04 | 37 |
| 21.2 | 4.19 | 42 |
| 22.3 | 3.99 | 58 |
| 23.2 | 3.83 | 26 |
| 23.7 | 3.75 | 37 |
| 25.1 | 3.548 | 26 |
| 25.3 | 3.520 | 32 |
| 26.3 | 3.389 | 26 |
| 27.5 | 3.243 | 42 |
| 28.6 | 3.121 | 53 |
| 28.8 | 3.100 | 53 |
| 29.6 | 3.018 | 32 |
| 31.9* | 2.805 | 26 |
| 32.8 | 2.730 | 42 |
| 34.5 | 2.600 | 21 |
| 35.0 | 2.564 | 21 |

TABLE XXXI-continued

| 2θ | d,(Å) | 100 × I/Io |
|---|---|---|
| 35.8 | 2.508 | 16 |

*impurity peak (c) The species denominated herein as CoAPSO-35 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)O_2$ and has a value of zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XXXII:

TABLE XXXII

| 2θ | d, (Å) | Relative Intensity |
|---|---|---|
| 10.9–11.0 | 8.12–8.04 | m–vs |
| 13.4–13.7 | 6.61–6.46 | m–vs |
| 17.3–17.4 | 5.13–5.10 | m–s |
| 20.9–21.2 | 4.25–4.19 | m |
| 21.9–22.3 | 4.06–3.99 | m–vs |
| 28.3–28.6 | 3.153–3.121 | m |

(d) The CoAPSO-35 compositions for which x-ray powder diffraction patterns have been obtained to date have patterns which are characterized by the x-ray pattern of Table XXXIII:

TABLE XXXIII

| 2θ | d, (Å) | 100 × I/Io |
|---|---|---|
| 7.9* | 11.19 | 8 |
| 8.6–8.7 | 10.28–10.16 | 18–26 |
| 10.9–11.0 | 8.12–8.04 | 45–90 |
| 11.6–11.8 | 7.63–7.50 | 8–21 |
| 13.4–13.7 | 6.61–6.46 | 30–100 |
| 15.9–16.2 | 5.57–5.47 | 15–16 |
| 17.3–17.4 | 5.13–5.10 | 26–83 |
| 17.6–17.8 | 5.04–5.98 | 20–37 |
| 20.9–21.2 | 4.25–4.19 | 42–58 |
| 21.9–22.3 | 4.06–3.99 | 58–100 |
| 22.7–23.2 | 3.92–3.83 | 13–26 |
| 23.3–23.7 | 3.83–3.75 | 37–38 |
| 24.9–25.1 | 3.58–3.548 | 13–26 |
| 25.3 | 3.520 | 32 |
| 25.6–26.3 | 3.480–3.389 | 8–26 |
| 26.9–27.5 | 3.314–3.243 | 28–42 |
| 28.3–28.6 | 3.153–3.121 | 45–53 |
| 28.8–29.6 | 3.100–3.018 | 13–53 |
| 31.4–31.9 | 2.849–2.805 | 10–26 |
| 32.2–32.8 | 2.780–2.730 | 40–42 |
| 34.3–34.5 | 2.614–2.600 | 10–21 |
| 35.0–35.2* | 2.564–2.550 | 8–21 |
| 35.8–35.9 | 2.508–2.501 | 8–16 |
| 37.8–37.9 | 2.380–2.374 | 5 |
| 39.4–39.5 | 2.287–2.281 | 5 |
| 41.9–42.0 | 2.156–2.151 | 8 |
| 42.6–42.7 | 2.122–2.118 | 10 |
| 44.6–44.7 | 2.032–2.027 | 8 |
| 47.8–47.9 | 1.903–1.900 | 8 |
| 48.6–48.7 | 1.873–1.870 | 8 |
| 49.8–49.9 | 1.831–1.828 | 10 |
| 51.2–51.3 | 1.784–1.781 | 10 |
| 55.6–55.7 | 1.653–1.650 | 8 |

EXAMPLE 117

(a) The as-synthesized CoAPSO-36 of example 93 was subjected to analysis by x-ray. The CoAPSO-36 product was characterized by the x-ray powder diffraction pattern of Table XXXIV below:

TABLE XXXIV

| 2θ | d, (Å) | 100 × I/Io |
|---|---|---|
| 7.3 | 12.11 | 7 |
| 8.0 | 11.12 | 100 |
| 8.2 | 10.74 | 29 |
| 9.2 | 9.65 | 4 |
| 12.9 | 6.86 | 5 |
| 13.6 | 6.52 | 8 |
| 13.7 | 6.48 | 8 |
| 15.9 | 5.57 | 14 |
| 16.5 | 5.38 | 42 |
| 18.4 | 4.83 | 6 |
| 19.1 | 4.64 | 37 |
| 20.8 | 4.27 | 49 |
| 21.6 | 4.12 | 7 |
| 21.8 | 4.09 | 22 |
| 22.1 | 4.03 | 28 |
| 22.6 | 3.94 | 29 |
| 23.0 | 3.86 | 9 |
| 24.0 | 3.71 | 9 |
| 27.3 | 3.267 | 20 |
| 27.7 | 3.226 | 7 |
| 28.4 | 3.148 | 13 |
| 28.7 | 3.116 | 5 |
| 29.2 | 3.063 | 12 |
| 30.4 | 2.940 | 7 |
| 32.1 | 2.792 | 12 |
| 34.9 | 2.571 | 12 |

(b) CoAPSO-36, of example 93 was calcined in air at 500° for one hour. The calcined product was characterized by the x-ray powder diffraction pattern of Table XXXV below:

TABLE XXXV

| 2θ | d, (Å) | 100 × I/Io |
|---|---|---|
| 7.4 | 12.00 | 8 |
| 8.0 | 11.10 | 100 |
| 8.3 | 10.69 | 33 |
| 13.6 | 6.52 | 13 |
| 15.9 | 5.58 | 8 |
| 16.6 | 5.36 | 32 |
| 19.3 | 4.59 | 29 |
| 20.8 | 4.27 | 26 |
| 21.5 | 4.14 | 8 |
| 21.8 | 4.07 | 11 |
| 22.3 | 3.98 | 19 |
| 22.7 | 3.92 | 17 |
| 24.0 | 3.71 | 7 |
| 27.3 | 3.266 | 19 |
| 27.8 | 3.215 | 10 |
| 28.3 | 3.154 | 12 |
| 28.4 | 3.145 | 13 |
| 28.5 | 3.131 | 10 |
| 29.2 | 3.062 | 13 |
| 32.0 | 2.797 | 10 |

(c) The species denominated herein as CoAPSO-36 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XXXVI:

TABLE XXXVI

| 2θ | d, (Å) | Relative Intensity |
|---|---|---|
| 7.8–8.0 | 11.33–11.05 | vs |
| 8.2–8.3 | 10.78–10.65 | m |
| 16.4–16.6 | 5.40–5.34 | m |
| 19.0–19.3 | 4.67–4.60 | m |
| 20.7–21.0 | 4.29–4.23 | m |
| 22.3–22.6 | 3.99–3.93 | w-m |

(d) The CoAPSO-36 compositions for which x-ray powder diffraction patterns have been obtained to date have patterns which are characterized by the x-ray pattern of Table XXXVII:

TABLE XXXVII

| 2θ | d, (Å) | 100 × I/Io |
|---|---|---|
| 7.3–7.5 | 12.11–11.79 | 7–8 |
| 7.8–8.0 | 11.33–11.05 | 100 |
| 8.2–8.3 | 10.78–10.65 | 29–33 |
| 9.2–9.3 | 9.61–9.51 | 4–5 |
| 12.9–13.0 | 6.86–6.81 | 4–5 |
| 13.5–13.6 | 6.56–6.51 | 8–13 |
| 13.7 | 6.46 | 7–8 |
| 15.8–16.0 | 5.61–5.54 | 8–14 |
| 16.4–16.6 | 5.40–5.34 | 32–42 |
| 18.4 | 4.82 | 4–6 |
| 19.0–19.3 | 4.67–4.60 | 29–36 |
| 20.7–21.0 | 4.29–4.23 | 26–49 |
| 21.5–21.7 | 4.13–4.10 | 7–8 |
| 21.8–22.0 | 4.08–4.04 | 11–22 |
| 22.3–22.6 | 3.99–3.93 | 17–29 |
| 22.9–23.0 | 3.88–3.87 | 5–9 |
| 23.9–24.0 | 3.72–3.71 | 7–9 |
| 27.2–27.3 | 3.278–3.267 | 19–20 |
| 27.6–27.8 | 3.232–3.209 | 7–10 |
| 28.3–28.4 | 3.153–3.143 | 12–13 |
| 28.5–28.7 | 3.132–3.110 | 5–10 |
| 29.0–29.2 | 3.079–3.058 | 12–13 |
| 30.3–30.4 | 2.950–2.940 | 5–7 |
| 32.0–32.1 | 2.797–2.788 | 10–12 |
| 34.7–34.9 | 2.585–2.571 | 10–12 |

EXAMPLE 118

(a) The as-synthesized CoAPSO-39 of example 45 was subjected to analysis by x-ray. The CoAPSO-39 product was characterized by the x-ray powder diffraction pattern of Table XXXVIII below:

TABLE XXXVIII

| 2θ | d, (Å) | 100 × I/Io |
|---|---|---|
| 8.0* | 11.05 | 31 |
| 9.4** | 9.41 | 47 |
| 13.1* | 6.76 | 22 |
| 13.3 | 6.66 | 16 |
| 14.8* | 5.99 | 9 |
| 15.6* | 5.68 | 31 |
| 16.2* | 5.47 | 6 |
| 18.1 | 4.90 | 16 |
| 19.0* | 4.67 | 9 |
| 20.2* | 4.40 | 41 |
| 21.0** | 4.23 | 100 |
| 22.1* | 4.02 | 53 |
| 22.4** | 3.97 | 53 |
| 22.6* | 3.93 | 69 |
| 23.1* | 3.85 | 66 |
| 24.7* | 3.60 | 13 |
| 26.4** | 3.376 | 28 |
| 26.9 | 3.314 | 13 |
| 27.7* | 3.220 | 13 |
| 28.1 | 3.175 | 13 |
| 28.6** | 3.121 | 25 |

TABLE XXXVIII-continued

| 2θ | d, (Å) | 100 × I/Io |
|---|---|---|
| 29.4 | 3.038 | 13 |
| 30.2 | 2.959 | 13 |
| 31.4* | 2.849 | 13 |
| 32.7** | 2.739 | 22 |
| 34.2** | 2.622 | 16 |
| 34.6 | 2.592 | 6 |
| 36.2 | 2.481 | 6 |
| 37.6 | 2.392 | 16 |
| 37.8** | 2.380 | 16 |
| 39.4** | 2.287 | 9 |
| 42.9** | 2.108 | 9 |
| 44.6** | 2.032 | 9 |
| 48.6 | 1.873 | 6 |
| 50.6* | 1.804 | 6 |
| 51.4 | 1.778 | 6 |
| 54.5** | 1.684 | 9 |
| 55.6** | 1.653 | 6 |

*peak resulting from CoAPSO-11
**peak resulting from CoAPSO-11 and CoAPSO 39

(b) The species denominated herein as CoAPSO-39 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XXXIX:

TABLE XXXIX

| 2θ | d, (Å) | Relative Intensity |
|---|---|---|
| 9.4–9.5 | 9.41–9.31 | m |
| 13.3–13.4 | 6.66–6.61 | m |
| 18.1–18.2 | 4.90–4.87 | w-m |
| 21.0–21.2 | 4.23–4.19 | vs |
| 22.4–22.5 | 3.97–3.95 | m-s |
| 26.4–26.5 | 3.376–3.363 | m |

(c) The CoAPSO-39 compositions for which x-ray powder diffraction patterns have been obtained to date have patterns which are characterized by the x-ray pattern of Table XXXX:

TABLE XXXX

| 2θ | d, (Å) | 100 × I/Io |
|---|---|---|
| 9.4–9.5 | 9.41–9.31 | 31–43 |
| 13.3–13.4 | 6.66–6.61 | 22–30 |
| 18.1–18.2 | 4.90–4.87 | 16–31 |
| 21.0–21.2 | 4.23–4.19 | 100 |
| 22.4–22.5 | 3.97–3.95 | 53–80 |
| 26.4–26.5 | 3.376–3.363 | 28–29 |
| 26.9–27.0 | 3.314–3.302 | 6–13 |
| 28.1–28.2 | 3.175–3.164 | 13–15 |
| 28.6–28.7 | 3.121–3.110 | 10–25 |
| 29.4–29.5 | 3.038–3.028 | 13–18 |
| 30.2 | 2.959 | 13–15 |
| 32.7–32.8 | 2.739–2.730 | 17–22 |
| 34.2–34.3 | 2.622–2.614 | 12–16 |
| 34.5–34.6 | 2.617–2.592 | 6–10 |
| 36.2–36.3 | 2.481–2.475 | 6–8 |
| 37.6–37.9 | 2.392–2.374 | 16–17 |
| 39.4–39.5 | 2.287–2.281 | 9–11 |
| 42.9–43.0 | 2.108–2.103 | 8–9 |
| 44.6–44.8 | 2.032–2.023 | 6–9 |
| 48.5–48.6 | 1.877–1.873 | 5–6 |
| 51.4–51.6 | 1.778–1.771 | 5–6 |
| 54.5–54.6 | 1.684–1.681 | 9–10 |
| 55.4–55.6 | 1.658–1.653 | 5–6 |

EXAMPLE 119

(a) The as-synthesized CoAPSO-44 of example 19 was subjected to analysis by x-ray. The CoAPSO-44 product was characterized by the x-ray powder diffraction pattern of Table XXXXI below:

TABLE XXXXI

| 2θ | d, (Å) | 100 × I/Io |
|---|---|---|
| 4.8* | 18.41 | 8 |
| 9.4 | 9.41 | 100 |
| 13.1 | 6.76 | 22 |
| 13.9 | 6.37 | 5 |
| 15.9 | 5.57 | (sh) |
| 16.2 | 5.47 | 37 |
| 17.4 | 5.10 | 5 |
| 19.0 | 4.67 | 9 |
| 20.8 | 4.27 | 72 |
| 21.8 | 4.08 | 17 |
| 22.7 | 3.92 | 9 |
| 23.1 | 3.85 | 9 |
| 24.4 | 3.65 | 49 |
| 26.2 | 3.401 | 31 |
| 27.8 | 3.209 | 11 |
| 29.0 | 3.079 | sh |
| 29.7 | 3.008 | 8 |
| 30.1 | 2.969 | 20 |
| 30.8 | 2.903 | 49 |
| 31.6 | 2.831 | 3 |
| 32.5 | 2.755 | 6 |
| 32.9 | 2.722 | 6 |
| 34.8 | 2.578 | 5 |
| 35.5 | 2.529 | 9 |
| 38.6 | 2.332 | 5 |
| 39.3 | 2.292 | 3 |
| 39.8 | 2.265 | sh |
| 40.0 | 2.254 | 6 |
| 42.2 | 2.141 | 5 |
| 42.6 | 2.122 | 5 |
| 43.7 | 2.071 | 3 |
| 44.4 | 2.040 | 3 |
| 46.2 | 1.965 | 3 |
| 47.3 | 1.922 | 3 |
| 48.2 | 1.888 | 12 |
| 48.7 | 1.870 | 8 |
| 50.3 | 1.814 | 15 |
| 52.0 | 1.759 | 5 |
| 53.8 | 1.704 | 9 |
| 54.8 | 1.675 | 3 |

(b) CoAPSO-44 of example 10 was calcined in air at 500° for 1.25 hours. The calcined product was characterized by the x-ray powder diffraction pattern of Table XXXXII below:

TABLE XXXXII

| 2θ | d, (Å) | 100 × I/Io |
|---|---|---|
| 8.9 | 9.94 | 20 |
| 9.3 | 9.51 | 100 |
| 12.9 | 6.86 | 24 |
| 14.0 | 6.33 | 5 |
| 15.8 | 5.61 | sh |
| 16.0 | 5.54 | 14 |
| 17.8 | 4.98 | 18 |
| 19.1 | 4.65 | 4 |
| 20.5 | 4.33 | 40 |
| 22.1 | 4.02 | 4 |
| 22.3 | 3.99 | 4 |
| 23.0 | 3.87 | 7 |
| 25.1 | 3.548 | 12 |

TABLE XXXXII-continued

| 2θ | d, (Å) | 100 × I/Io |
|---|---|---|
| 25.8 | 3.453 | 13 |
| 27.6 | 3.232 | 3 |
| 28.2 | 3.164 | 4 |
| 29.5 | 3.028 | 3 |
| 30.6 | 2.921 | 21 |
| 31.1 | 2.876 | 14 |
| 31.7 | 2.823 | 4 |
| 32.2 | 2.780 | 2 |
| 33.4 | 2.683 | 3 |
| 33.7 | 2.660 | 4 |
| 34.5 | 2.600 | 8 |
| 36.2 | 2.481 | 5 |
| 38.2 | 2.356 | 2 |
| 38.7 | 2.327 | 3 |
| 39.2 | 2.298 | 2 |
| 39.8 | 2.265 | 3 |
| 42.9 | 2.108 | 3 |
| 43.4 | 2.085 | 4 |
| 47.6 | 1.910 | 3 |
| 49.0 | 1.859 | 5 |
| 49.8 | 1.831 | 3 |
| 50.6 | 1.804 | 3 |
| 51.0 | 1.791 | 4 |
| 53.2 | 1.722 | 3 |
| 54.7 | 1.678 | 2 |

(c) The species denominated herein as CoAPSO-44 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XXXXIII:

TABLE XXXXIII

| 2θ | d, (Å) | Relative Intensity |
|---|---|---|
| 9.3–9.5 | 9.51–9.31 | vs |
| 16.0–16.3 | 5.54–5.44 | w–m |
| 20.5–20.8 | 4.33–4.27 | m |
| 24.3–25.1 | 3.66–3.548 | w–m |
| 25.8–26.2 | 3.453–3.401 | w–m |
| 30.7–31.1 | 2.912–2.876 | vw–m |

(d) The CoAPSO-44 compositions for which x-ray powder diffraction patterns have been obtained to date have patterns which are characterized by the x-ray pattern of Table XXXXIV:

TABLE XXXXIV

| 2θ | d, (Å) | 100 × I/Io |
|---|---|---|
| 4.8* | 18.41 | 8 |
| 8.9 | 9.94 | 20 |
| 9.3–9.5 | 9.51–9.31 | 100 |
| 12.9–13.1 | 6.86–6.76 | 22–24 |
| 13.7–14.0 | 6.46–6.33 | 5–6 |
| 15.8–15.9 | 5.6–5.57 | sh |
| 16.0–16.3 | 5.54–5.44 | 14–37 |
| 17.4–17.8 | 5.10–4.98 | 5–18 |
| 18.9–19.1 | 4.70–4.65 | 4–9 |
| 20.5–20.8 | 4.33–4.27 | 40–72 |
| 21.8–22.1 | 4.08–4.02 | 4–17 |
| 22.3–22.7 | 3.99–3.92 | 4–9 |
| 23.0–23.1 | 3.87–3.85 | 7–9 |
| 24.3–25.1 | 3.66–3.548 | 12–49 |
| 25.8–26.2 | 3.453–3.401 | 13–31 |
| 27.6–27.8 | 3.232–3.209 | 3–11 |
| 28.2 | 3.164 | 4 |
| 29.0–29.5 | 3.079–3.028 | sh–3 |
| 29.7–30.6 | 3.008–2.921 | 8–21 |
| 30.7–31.1 | 2.912–2.876 | 4–49 |
| 31.6–31.7 | 2.831–3.823 | 3–4 |
| 32.2 | 2.780 | 2 |
| 32.5–33.7 | 2.755–2.660 | 3–6 |
| 34.5–34.8 | 2.600–2.578 | 5–8 |
| 35.4–36.2 | 2.536–2.481 | 5–9 |
| 38.2–38.6 | 2.356–2.332 | 2–5 |
| 38.7–39.3 | 2.327–2.292 | 2–3 |
| 39.8–40.0 | 2.265–2.254 | sh–3 |
| 42.2–42.9 | 2.141–2.108 | 3–5 |
| 43.4–43.7 | 2.085–2.071 | 3–4 |
| 44.4–46.2 | 2.040–1.965 | 3 |
| 47.3–47.6 | 1.922–1.910 | 3 |
| 48.1–49.0 | 1.892–1.859 | 5–12 |
| 49.8–50.3 | 1.831–1.814 | 3–15 |
| 50.6 | 1.804 | 3 |
| 51.0–52.0 | 1.791–1.759 | 4–5 |
| 53.2–53.8 | 1.722–1.704 | 3–9 |
| 54.7–54.8 | 1.678–1.675 | 2–3 |

EXAMPLE 120

(a) The as-synthesized CoAPSO-46 of example 36 was subjected to analysis by x-ray. The CoAPSO-46 product was characterized by the x-ray powder diffraction pattern of Table XXXXV below:

TABLE XXXXV

| 2θ | d, (Å) | 100 × I/Io |
|---|---|---|
| 6.6 | 13.39 | 11 |
| 6.9 | 12.81 | 7 |
| 7.2 | 12.28 | 12 |
| 7.7 | 11.48 | 100 |
| 12.5 | 7.08 | 7 |
| 13.1 | 6.76 | 5 |
| 13.3 | 6.66 | 6 |
| 13.5 | 6.56 | 4 |
| 15.0 | 5.91 | 4 |
| 15.4 | 5.75 | 5 |
| 16.1 | 5.51 | 3 |
| 16.8 | 5.28 | 6 |
| 17.4 | 5.10 | 4 |
| 17.5 | 5.07 | 5 |
| 19.9 | 4.46 | 5 |
| 20.6 | 4.31 | 5 |
| 21.0 | 4.23 | 4 |
| 21.4 | 4.15 | sh |
| 21.7 | 4.10 | 13 |
| 22.2 | 4.00 | 3 |
| 22.9 | 3.88 | 7 |
| 23.8 | 3.74 | 4 |
| 24.3 | 3.66 | 5 |
| 26.3 | 3.389 | 3 |
| 26.9 | 3.314 | 7 |
| 27.8 | 3.209 | 10 |
| 28.3 | 3.153 | 5 |
| 28.8 | 3.010 | 6 |
| 29.9 | 2.988 | 4 |
| 30.2 | 2.959 | 4 |
| 30.7 | 2.912 | 4 |
| 30.9 | 2.894 | 4 |
| 31.2 | 2.867 | 5 |
| 31.8 | 2.814 | 3 |
| 33.0 | 2.714 | 4 |
| 34.2 | 2.622 | 3 |
| 36.0 | 2.495 | 5 |
| 36.6 | 2.455 | 3 |
| 44.0 | 2.058 | 3 |

(b) The species denominated herein as CoAPSO-46 has a three-dimensional microporous crystal framework structure of $CoO_2$, $AlO_2$, $PO_2$ and $SiO_2$ tetrahedral units and has an empirical chemical composition on an anhydrous basis expressed by the formula:

$$mR:(Co_wAl_xP_ySi_x)O_2$$

where "R" represents at least one organic templating agent present in the intracrystalline pore system; "m" represents the molar amounts of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table XXXXVI:

TABLE XXXXVI

| 2θ | d, (Å) | Relative Intensity |
|---|---|---|
| 6.5–6.7 | 13.60–13.19 | w |
| 7.2–7.4 | 12.28–11.95 | w |
| 7.6–7.8 | 11.63–11.33 | vs |
| 21.6–21.7 | 4.11–4.10 | w |
| 27.8–27.9 | 3.209–3.198 | w |

(c) The CoAPSO-46 compositions for which x-ray powder diffraction patterns have been obtained to date have patterns which are characterized by the x-ray pattern of Table XXXXVII:

TABLE XXXXVII

| 2θ | d,(Å) | 100 × I/Io |
|---|---|---|
| 6.5–6.7 | 13.60–13.19 | 11 |
| 6.9–7.0 | 12.81–12.63 | 7 |
| 7.2–7.4 | 12.28–11.95 | 12 |
| 7.6–7.8 | 11.63–11.33 | 100 |
| 12.5–12.6 | 7.08–7.03 | 7 |
| 13.1–13.3 | 6.76–6.66 | 5 |
| 13.5–13.9 | 6.56–6.37 | 4 |
| 15.0–15.1 | 5.91–5.87 | 4 |
| 15.4 | 5.75 | 5 |
| 16.1 | 5.51 | 3 |
| 16.7–16.8 | 5.31–5.28 | 6 |
| 17.4–17.5 | 5.10–5.07 | 4 |
| 19.9–20.0 | 4.46–4.44 | 5 |
| 20.5–20.6 | 4.33–4.31 | 5 |
| 21.0 | 4.23 | 4 |
| 21.4 | 4.15 | sh |
| 21.6–21.7 | 4.11–4.10 | 13 |
| 22.1–22.2 | 4.02–4.00 | 3 |
| 22.8–22.9 | 3.90–3.88 | 7 |
| 23.8 | 3.74 | 4 |
| 24.2–24.3 | 3.68–3.66 | 5 |
| 26.3–26.4 | 3.389–3.376 | 3 |
| 26.8–26.9 | 3.326–3.314 | 7 |
| 27.8–27.9 | 3.209–3.198 | 10 |
| 28.3–28.4 | 3.153–3.143 | 5 |
| 28.8–28.9 | 3.010–3.089 | 6 |
| 29.8–29.9 | 2.998–2.988 | 4 |
| 30.2 | 2.959 | 4 |
| 30.7 | 2.912 | 4 |
| 30.9–31.0 | 2.894–2.885 | 4 |
| 31.2–31.3 | 2.867–2.858 | 5 |
| 31.8–31.9 | 2.814–2.805 | 3 |
| 32.8–33.0 | 2.730–2.714 | 4 |
| 34.2–34.3 | 2.622–2.614 | 3 |
| 35.9–36.0 | 2.510–2.495 | 5 |
| 36.5–36.6 | 2.462–2.455 | 3 |
| 44.0–44.1 | 2.058–2.053 | 3 |

EXAMPLE 121

(a) The as-synthesized CoAPSO-47 of example 104 was subjected to analysis by x-ray. The CoAPSO-47 product was characterized by the x-ray powder diffraction pattern of Table XXXXVIII below:

TABLE XXXXVIII

| 2θ | d,(Å) | 100 × I/Io |
|---|---|---|
| 9.4 | 9.37 | 94 |
| 12.9 | 6.88 | 16 |
| 13.8 | 6.40 | 9 |
| 16.0 | 5.55 | 40 |
| 17.5 | 5.06 | 14 |
| 18.9 | 4.69 | 6 |
| 20.6 | 4.32 | 100 |
| 21.8 | 4.08 | 11 |
| 22.4 | 3.97 | 4 |
| 23.0 | 3.87 | 12 |
| 24.6 | 3.62 | 38 |
| 25.9 | 3.443 | 22 |
| 27.6 | 3.230 | 11 |
| 29.5 | 3.030 | 6 |
| 30.6 | 2.926 | 42 |
| 31.5 | 2.844 | 3 |
| 33.1 | 2.707 | 3 |
| 34.5 | 2.602 | 9 |
| 35.7 | 2.518 | 7 |
| 38.4 | 2.345 | 4 |
| 39.6 | 2.275 | 4 |
| 42.5 | 2.128 | 4 |
| 47.6 | 1.910 | 4 |
| 48.5 | 1.877 | 11 |
| 50.3 | 1.815 | 7 |
| 52.3 | 1.749 | 2 |
| 53.2 | 1.721 | 5 |
| 53.9 | 1.700 | 3 |
| 54.3 | 1.690 | 3 |

(b) CoAPSO-47, of example 104 was calcined in air at 500° for 1.5 hours. The calcined product was characterized by the x-ray powder diffraction pattern of Table XXXXIX below:

TABLE XXXXIX

| 2θ | d,(Å) | 100 × I/Io |
|---|---|---|
| 9.6 | 9.18 | 100 |
| 3.1 | 6.77 | 26 |
| 14.2 | 6.23 | 3 |
| 16.3 | 5.44 | 10 |
| 18.1 | 4.90 | 16 |
| 19.4 | 4.58 | 3 |
| 21.0 | 4.24 | 26 |
| 22.5 | 3.96 | 3 |
| 23.5 | 3.79 | 3 |
| 25.5 | 3.499 | 11 |
| 26.4 | 3.381 | 9 |
| 28.7 | 3.113 | 4 |
| 31.2 | 2.868 | 14 |
| 31.7 | 2.824 | 6 |

(c) The species denominated herein as CoAPSO-47 has a three-dimensional microporous crystal framework structure of $CoO_2$, $AlO_2$, $PO_2$ and $SiO_2$ tetrahedral units and has an empirical chemical compositions on an anhydrous basis expressed by the formula:

$$mR:(Co_wAl_xP_ySi_z)O_2$$

where "R" represents at least one organic templating agent present in the intracrystalline pore system; "m" represents the molar amount of "R" per mole of $(Co_wAl_xP_ySi_z)O_2$ and has a value of from zero to about 0.3; "w", "x", "y" and "z" represent the mole fractions as above defined with reference to FIG. 1 or FIG. 2; and having in the as-synthesized or calcined form a characteristic x-ray powder diffraction pattern which contains at least the d-spacings set forth in Table LI:

TABLE LI

| 2θ | d,(Å) | Relative Intensity |
|---|---|---|
| 9.4–9.6 | 9.41–9.21 | vs |

TABLE LI-continued

| 2θ | d,(Å) | Relative Intensity |
|---|---|---|
| 12.8–13.1 | 6.92–6.76 | w-m |
| 16.0–16.3 | 5.54–5.44 | w-m |
| 20.6–21.0 | 4.31–4.23 | m-vs |
| 25.5–25.9 | 3.493–3.440 | w-m |
| 30.6–31.1 | 2.921–2.876 | w-m |

(d) The CoAPSO-47 compositions for which x-ray powder diffraction patterns have been obtained to date have patterns which are characterized by the x-ray pattern of Table LII:

TABLE LII

| 2θ | d,(Å) | 100 × I/Io |
|---|---|---|
| 9.4–9.6 | 9.41–9.21 | 94–100 |
| 12.8–13.1 | 6.92–6.76 | 16–26 |
| 13.8–14.2 | 6.42–6.24 | 3–9 |
| 16.0–16.3 | 5.54–5.44 | 10–40 |
| 17.5–18.1 | 5.07–4.90 | 14–16 |
| 18.9–19.4 | 4.70–4.58 | 3–6 |
| 20.6–21.0 | 4.31–4.23 | 26–100 |
| 21.8 | 4.08 | 11 |
| 22.4–22.5 | 3.97–3.95 | 3–4 |
| 23.0–23.5 | 3.87–3.79 | 3–12 |
| 24.6 | 3.62 | 38 |
| 25.5–25.9 | 3.493–3.440 | 11–22 |
| 26.4 | 3.376 | 9 |
| 27.6 | 3.232 | 11 |
| 28.7 | 3.110 | 4 |
| 29.5 | 3.028 | 6 |
| 30.6–31.1 | 2.921–2.876 | 13–42 |
| 31.5–31.7 | 2.840–2.823 | 3–6 |
| 33.1 | 2.706 | 3 |
| 34.5 | 2.600 | 9 |
| 35.7 | 2.515 | 7 |
| 38.4 | 2.344 | 4 |
| 39.6 | 2.276 | 4 |
| 42.5 | 2.127 | 4 |
| 47.6 | 1.910 | 4 |
| 48.5 | 1.877 | 11 |
| 50.3 | 1.814 | 7 |
| 52.3 | 1.749 | 2 |
| 53.2 | 1.722 | 5 |
| 53.9 | 1.701 | 3 |
| 54.3 | 1.689 | 3 |

EXAMPLE 122

In order to demonstrate the catalytic activity of the CoAPSO compositions, calcined samples of the CoAPSO products were tested for catalytic cracking by n-butane cracking.

The n-butane cracking was carried out using a bench scale rector. The reactor was a cylindrical quartz tube 254 mm. in length and 10.3 mm. I.D. In each test the reactor was loaded with particles of the test CoAPSO's which were 20–40 mesh. (U.S. std.) in size and in an amount of from 0.5 to 5 grams, the quantity being selected so that the conversion of n-butane was at least 5% and not more than 90% under the test conditions. Most of the CoAPSO had been previously calcined in air to remove organic materials from the pore system, and were activated in situ in the reactor in a flowing stream of helium at 500° C. for one hour. In some instances, samples were calcined in situ. The feedstock was a helium-n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation.

The pseudo-first-order rate constant ($k_A$) was calculated to determine the relative catalytic activity of the CoAPSO compositions. The $k_A$ value (cm$^3$/g min) obtained for the CoAPSO compositions are set forth, below.

| CoAPSO of Example No: | Rate Constant ($k_A$) |
|---|---|
| CoAPSO-11 (Ex. 50) | 1.0 |
| CoAPSO-11 (Ex. 42)* | 2.0 |
| CoAPSO-11 (Ex. 42) | 1.9 |
| CoAPSO-11 (Ex. 61) | 1.4 |
| CoAPSO-31 (Ex. 102) | 2.1 |
| CoAPSO-34 (Ex. 89)* | 1.5 |
| CoAPSO-34 (Ex. 89) | 8.7 |
| CoAPSO-34 (Ex. 90) | 11.8 |
| CoAPSO-34 (Ex. 83) | 28.1 |
| CoAPSO-34 (Ex. 77)* | 11.1 |
| CoAPSO-35 (Ex. 10)* | 1.0 |
| CoAPSO-44 (Ex. 19) | 18.1 |
| CoAPSO-46 (Ex. 36) | 2.4 |
| CoAPSO-47 (Ex. 104) | 2.3 |
| CoAPSO-44 (Ex. 19)* | 2.7 |
| CoAPSO-36 (Ex. 93)* | 1.0 |
| CoAPSO-34 (Ex. 83)* | 4.1 |
| CoAPSO-34 (Ex. 69)* | 9.4 |
| CoAPSO-34 (Ex. 79)* | 5.2 |
| CoAPSO-34 (Ex. 78)* | 4.6 |
| CoAPSO-34 (Ex. 81)* | 3.3 |

*calcined in situ at 500° C. in helium for 2 hours prior to activation.

PROCESS APPLICATIONS

The CoAPSO compositions of the present invention are, in general, hydrophilic and adsorb water preferentially over common hydrocarbon molecules such as paraffins, olefins and aromatic species, e.g., benzene, xylenes and cumene. Thus, the CoAPSOs as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These CoAPSOs are therefore suitably employed in the drying of reformer hydrogen streams and in the drying of oxygen, nitrogen or air prior to liquidification.

The present CoAPSO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalyst compositions having silica or alumina bases. Of the general class, those species having pores larger than about 4 Å are preferred for catalytic applications.

Among the hydrocarbon conversion reactions catalyzed by CoAPSO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using CoAPSO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The CoAPSO catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerizations processes in which feedstocks such a normal paraffins are converted to saturated branched chain isomers. Hydroisomerization is carried out at a temperature of from about 200° F. to 600° F., preferably 300° F. to 550° F. with an LHSV value of from about 0.2 to 1.0. Hydrogen is supplied to the reactor in admixture with the hydrocarbon feedstock in molar proportions (hydrogen to hydrocarbon) of between 1 and 5.

At somewhat higher temperatures i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of $C_7$-$C_{20}$. Contact time between the feedstock and the catalyst is generally relatively short to avoid undesirable side reactions such a olefin polymerization and paraffin cracking. LHSV values in the range of 0.1 to 10, preferably 1.0 to 6.0 are suitable.

The unique crystal structure of the present CoAPSO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F., pressures in the range of 100 to 2000 p.s.i.g. and LHSV values in the range of 0.1 to 15.

Catalytic cracking processes are preferably carried out with CoAPSO compositions using feedstocks such as gas oils, heavy naphthas, deasphalted crude oil residua, etc., with gasoline being the principal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the CoAPSO catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°-1000° F. are employed at moderate hydrogen pressures of about 300-1000 p.s.i.g., other conditions being similar to those described above for catalytic hydrocracking. Preferred catalyst are of the same type described above in connection with catalytic dehydrocyclization. Particlarly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constitutents markedly inhibits the activity of hydrocracking catalysts. Consequently, it is necessary to operate at more extreme conditions when it is desired to obtain the same degree of hydrocracking conversion per pass on a relatively nitrogenous feed than are required with a feed containing less organonitrogen compounds. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°-900° F., while paraffins, naphthenes and alkyl aromatics are isomerized at temperatures of 700°-1000° F. Particularly desirable isomerization reactions contemplated herein include the conversion of n-heptene and/or n-octane to isoheptanes iso-octanes, butane to iso-butane, methylcyclopentane to cyclohexane, meta-xylene and/or ortho-xylene to paraxylene, 1-butene to 2-butene and/or isobutene, n-hexene to isohexene, cyclohexene to methylcyclopentene etc. The preferred form of the catalyst is a combination of the CoAPSO with polyvalent metal compounds (such as sulfides) of metals of Group II-A, Group II-B and rare earth metals. For alkylation and dealkylation processes the CoAPSO compositions having pores of at least 5 Å are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In the alkylation of benzene, toluene and xylene, the preferred alkylating agents are olefins such as ethylene and propylene.

We claim:

1. Process for converting a hydrocarbon which comprises contacting said hydrocarbon under hydrocarbon converting conditions with a molecular sieve, said molecular sieve being a crystalline molecular sieve having three-dimensional microporous framework structures of $CoO_2$, $AlO_2$, $PO_2$ and $SiO_2$ tetrahedral units having an empirical chemical composition on an anhydrous basis expressed by the formula:

$$mR:(Co_wAl_xP_ySi_z)O_2$$

wherein "R" represents at least one organic templating agent present in the intracrystalline pore system; "m" represents the molar amount of "R" present per mole of $(Co_xAl_xP_ySi_z)O_2$ and has a value between zero (0) and about 0.3; and "w", "x", "y" and "z" represent the mole fractions of cobalt, aluminum, phosphorus and silicon, respectively, present at tetrahedral oxides, said mole fractions being such that they are within the pentagonal compositional area defined by points A, B, C, D, and E of FIG. 1 and each has a value of at least 0.01.

2. Process according to claim 1 wherein the hydrocarbon conversion process is cracking.

3. Process according to claim 1 wherein the hydrocarbon conversion process is hydrocracking.

4. Process according to claim 1 wherein the hydrocarbon conversion process is hydrogenation.

5. Process according to claim 1 wherein the hydrocarbon conversion process is polymerization.

6. Process according to claim 1 wherein the hydrocarbon conversion process is alkylation.

7. Process according to claim 1 wherein the hydrocarbon conversion process is reforming.

8. Process according to claim 1 wherein the hydrocarbon conversion process is hydrotreating.

9. Process according to claim 1 wherein the hydrocarbon conversion process is isomerization.

10. Process according to claim 9 wherein the isomerization conversion process is xylene isomerization.

11. Process according to claim 1 wherein the hydrocarbon conversion process is dehydrocyclization.

12. Process according to claim 1 wherein the mole fractions of cobalt, aluminum, phosphorus and silicon present as tetrahedral oxides in said crystalline molecular sieve are within the tetragonal compositional area defined by points a, b, c and d of FIG. 2.

13. Process according to claim 1 wherein the mole fractions "w" and "z" of cobalt and silicon respectively in said crystalline molecular sieve satisfy the following relationships:

$$w \geq 0.01$$

$$z \geq 0.02.$$

14. Process according to claim 1 wherein, before being contacted with said mixture of molecular species, said molecular sieve is calcined at a temperature sufficiently high to remove at least some of any organic templating agent present in the intracrystalline pore system.

15. Process according to claim 1 wherein said crystalline molecular sieve has a characteristic X-ray powder diffraction pattern which contains at least the d-spacings set forth in one of the following Tables A to H and J to M:

TABLE A

| | (CoAPSO-5) | |
|---|---|---|
| 2θ | d(Å) | Relative Intensity |
| 7.3–7.5 | 12.11–11.79 | m–vs |
| 14.7–14.9 | 6.03–5.95 | w–m |
| 19.6–19.8 | 4.53–4.48 | w–m |
| 20.9–21.2 | 4.25–4.19 | w–vs |
| 22.3–22.4 | 3.99–3.97 | m–vs |
| 25.8–26.0 | 3.453–3.427 | vw–m |

TABLE B

| | (CoAPSO-11) | |
|---|---|---|
| 2θ | d(Å) | Relative Intensity |
| 7.9–8.1 | 11.19–10.92 | m |
| 9.3–9.5 | 9.51–9.31 | m–s |
| 21.0–21.3 | 4.23–4.17 | vs |
| 22.1–22.3 | 4.02–3.99 | m |
| 22.7–23.1 | 3.92–3.85 | m |
| 23.2–23.4 | 3.83–3.80 | m |

TABLE C

| | (CoAPSO-16) | |
|---|---|---|
| 2θ | d(Å) | Relative Intensity |
| 11.4–11.6 | 7.76–7.63 | w–s |
| 17.2–17.4 | 5.16–5.10 | m |
| 18.7–18.9 | 4.75–4.70 | vw–m |
| 21.9–22.1 | 4.06–4.02 | vs |
| 23.1–23.3 | 3.85–3.82 | m |
| 26.8–27.0 | 3.326–3.302 | m |
| 29.8–29.9 | 2.998–2.988 | w–m |

TABLE D

| | (CoAPSO-20) | |
|---|---|---|
| 2θ | d(Å) | Relative Intensity |
| 13.9–14.0 | 6.37–6.33 | m |
| 19.7–19.8 | 4.51–4.48 | m |
| 24.2–24.3 | 3.68–3.66 | vs |
| 28.0–28.1 | 3.187–3.175 | w |
| 31.4–31.5 | 2.849–2.840 | w |
| 34.5–34.6 | 2.600–2.592 | w |

TABLE E

| | (CoAPSO-31) | |
|---|---|---|
| 2θ | d(Å) | Relative Intensity |
| 8.5–8.6 | 10.40–10.28 | m |
| 20.2–20.3 | 4.40–4.37 | m |
| 22.0–22.1 | 4.04–4.02 | m |
| 22.6–22.7 | 3.93–3.92 | vs |
| 28.0–28.1 | 3.187–3.175 | w |
| 31.7–31.8 | 2.823–2.814 | m |

TABLE F

| | (CoAPSO-34) | |
|---|---|---|
| 2θ | d(Å) | Relative Intensity |
| 9.4–9.8 | 9.41–9.03 | s–vs |
| 12.86–13.06 | 6.86–6.76 | w |
| 14.08–14.30 | 6.28–6.19 | w–m |
| 15.90–16.20 | 5.57–5.47 | vw–m |
| 20.60–20.83 | 4.31–4.26 | w–vs |
| 30.50–30.80 | 2.931–2.903 | w–m |

TABLE G

| | (CoAPSO-35) | |
|---|---|---|
| 2θ | d(Å) | Relative Intensity |
| 10.9–11.0 | 8.12–8.04 | m–vs |
| 13.4–13.7 | 6.61–6.46 | m–vs |
| 17.3–17.4 | 5.13–5.10 | m–s |
| 20.9–21.2 | 4.25–4.19 | m |
| 21.9–22.3 | 4.06–3.99 | m–vs |
| 28.3–28.6 | 3.153–3.121 | m |

TABLE H

| | (CoAPSO-36) | |
|---|---|---|
| 2θ | d(Å) | Relative Intensity |
| 7.8–8.0 | 11.33–11.05 | vs |
| 8.2–8.3 | 10.78–10.65 | m |
| 16.4–16.6 | 5.40–5.34 | m |
| 19.0–19.3 | 4.67–4.60 | m |
| 20.7–21.0 | 4.29–4.23 | m |
| 22.3–22.6 | 3.99–3.93 | w–m |

TABLE J

| | (CoAPSO-39) | |
|---|---|---|
| 2θ | d(Å) | Relative Intensity |
| 9.4–9.5 | 9.41–9.31 | m |
| 13.3–13.4 | 6.66–6.61 | m |
| 18.1–18.2 | 4.90–4.87 | w–m |
| 21.0–21.2 | 4.23–4.19 | vs |
| 22.4–22.5 | 3.97–3.95 | m–s |
| 26.4–26.5 | 3.376–3.363 | m |

TABLE K

| | (CoAPSO-44) | |
|---|---|---|
| 2θ | d(Å) | Relative Intensity |
| 9.3–9.5 | 9.51–9.31 | vs |
| 16.0–16.3 | 5.54–5.44 | w–m |
| 20.5–20.8 | 4.33–4.27 | m |
| 24.3–25.1 | 3.66–3.548 | w–m |
| 25.8–26.2 | 3.453–3.401 | w–m |
| 30.7–31.1 | 2.912–2.876 | vw–m |

TABLE L

| | (CoAPSO-46) | |
|---|---|---|
| 2θ | d(Å) | Relative Intensity |
| 6.5–6.7 | 13.60–13.19 | w |
| 7.2–7.4 | 12.28–11.95 | w |
| 7.6–7.8 | 11.63–11.33 | vs |
| 21.6–21.7 | 4.11–4.10 | w |
| 27.8–27.9 | 3.209–3.198 | w |

TABLE M

| | (CoAPSO-47) | |
|---|---|---|
| 2θ | d(Å) | Relative Intensity |
| 9.4–9.6 | 9.41–9.21 | vs |
| 12.8–13.1 | 6.92–6.76 | w–m |
| 16.0–16.3 | 5.54–5.44 | w–m |
| 20.6–21.0 | 4.31–4.23 | m–vs |
| 25.5–25.9 | 3.493–3.440 | w–m |
| 30.6–31.1 | 2.921–2.876 | w–m. |

* * * * *